United States Patent
Li et al.

(10) Patent No.: US 10,526,392 B2
(45) Date of Patent: Jan. 7, 2020

(54) SYNTHETIC BIOLOGY-BASED ADCC TECHNOLOGY

(71) Applicant: 1GLOBE BIOMEDICAL CO., LTD., Beijing (CN)

(72) Inventors: Chiang J. Li, Cambridge, MA (US); Shyam Unniraman, Newton, MA (US)

(73) Assignee: 1GLOBE BIOMEDICAL CO., LTD., Beijing (CN)

( * ) Notice: Subject to any disclaimer, the term of this patent is extended or adjusted under 35 U.S.C. 154(b) by 86 days.

(21) Appl. No.: 15/110,057

(22) PCT Filed: Jan. 8, 2015

(86) PCT No.: PCT/US2015/010708
§ 371 (c)(1),
(2) Date: Jul. 6, 2016

(87) PCT Pub. No.: WO2015/106043
PCT Pub. Date: Jul. 16, 2015

(65) Prior Publication Data
US 2016/0355566 A1    Dec. 8, 2016

Related U.S. Application Data

(60) Provisional application No. 61/925,217, filed on Jan. 8, 2014.

(51) Int. Cl.
| | |
|---|---|
| C07H 21/04 | (2006.01) |
| C12N 15/00 | (2006.01) |
| C12N 15/63 | (2006.01) |
| C07K 14/735 | (2006.01) |
| C07K 14/725 | (2006.01) |
| C07K 14/705 | (2006.01) |
| A61K 35/17 | (2015.01) |
| C07K 14/715 | (2006.01) |
| A61K 48/00 | (2006.01) |

(52) U.S. Cl.
CPC ........ *C07K 14/70535* (2013.01); *A61K 35/17* (2013.01); *C07K 14/7051* (2013.01); *C07K 14/70503* (2013.01); *C07K 14/70521* (2013.01); *C07K 14/70575* (2013.01); *C07K 14/70578* (2013.01); *C07K 14/7153* (2013.01); *A61K 48/005* (2013.01); *C07K 2319/03* (2013.01); *C07K 2319/70* (2013.01)

(58) Field of Classification Search
CPC ........ C07K 14/70535; C07K 14/70503; C07K 2319/03; C07K 2319/70; A61K 48/005
See application file for complete search history.

(56) References Cited

U.S. PATENT DOCUMENTS

| | | | |
|---|---|---|---|
| 5,359,046 A | 10/1994 | Capon et al. | |
| 2005/0142120 A1 | 6/2005 | Keler et al. | |
| 2008/0213216 A1 | 9/2008 | Schreiber et al. | |
| 2010/0035280 A1 | 2/2010 | Kawai | |
| 2013/0071414 A1* | 3/2013 | Dotti | C12N 5/0636 424/184.1 |

FOREIGN PATENT DOCUMENTS

| | | |
|---|---|---|
| EP | 2309263 B1 | 6/2015 |
| WO | 2007041635 A2 | 4/2007 |
| WO | WO-2015106043 A2 | 7/2015 |
| WO | WO-2015106043 A3 | 7/2015 |

OTHER PUBLICATIONS

Krause et al, "Antigen-dependent CD28 Signaling Selectively Enhances Survival and Proliferation in Genetically Modified Activated Human Primary T Lymphocytes," J. Exp. Med., 1998, 188:619-26.
Finney et al.,"Activation of Resting Human Primary T Cells with Chimeric Receptors: Costimulation from CD28, Inducible Costimulator, CD134, and CD137 in Series with Signals from the TCRz Chain," J Immunol., 2004, 172:104-113.
Johnson et al. "Gene therapy with human and mouse T-cell receptors mediates cancer regression and targets normal tissues expressing cognate antigen," Blood, 2009, 114, 535-46.
Hu et al., "Treatment with CD20-specific antibody prevents and reverses autoimmune diabetes in mice," J Clin Invest. 2007, 117(12): 3857-67.
Xiu et al. "B Lymphocyte Depletion by CD20 Monoclonal Antibody Prevents Diabetes in Nonobese Diabetic Mice despite Isotype-Specific Differences in Fc gR Effector Functions," J Immunol. 2008, 180(5): 2863-75.
Barr et al. "B cell depletion therapy ameliorates autoimmune disease through ablation of IL-6-producing B cells," J Exp Med. 2012, 209(5): 1001-10.
Yanaba et al., "B Cell Depletion Delays Collagen-Induced Arthritis in Mice: Arthritis Induction Requires Synergy between Humoral and Cell-Mediated Immunity," J Immunol. 2007, 179(2): 1369-80.
Klein et al., "HIV therapy by a combination of broadly neutralizing antibodies in humanized mice," Nature, 2012, 492 (7427): 118-22.
Jaworski et al. "Neutralizing Polyclonal IgG Present during Acute Infection Prevents Rapid Disease Onset in Simian-Human Immunodeficiency Virus SHIVSF162P3-Infected Infant Rhesus Macaques," J Virol. 2013, 87(19): 10447-59.
Wilson et al., "HIV-1-Specific CTL Responses Primed In Vitro by Blood-Derived Dendritic Cells and Th1-Biasing Cytokines," J Immunol., 1999, 162: 3070-78.
Shultz et al., "Humanized mice in translational biomedical research," Nat Rev Immunol. Feb. 2007; 7(2) 118-30.

(Continued)

*Primary Examiner* — Quang Nguyen
(74) *Attorney, Agent, or Firm* — Milstein Zhang & Wu LLC; Duan Wu, Esq.

(57) ABSTRACT

A novel synthetic biology-based ADCC technology is provided that enhances or enables ADCC response. The novel ADCC technology can be used to prevent or treat cancers, infectious, inflammatory or autoimmune diseases, and other diseases where elimination of diseased cells is desirable.

3 Claims, 14 Drawing Sheets
Specification includes a Sequence Listing.

(56) References Cited

OTHER PUBLICATIONS

Van De Winkel et al. "Gene Organization of the Human High Affinity Receptor for IgG Fc [gramma] RI (CD64)," J of Biological Chemistry. Jul. 15, 1991. vol. 266. No. 20.

Thiel V et al. "Multigene RNA Vector Based on Coronavirus Transcription," Journal of Virology, Sep. 2003. vol. 77. No. 18, pp. 9790-9798.

Allen, JM. et al. "Nucleotide Sequence of Three Cdnas for the Human High Affinity Fc Receptor (FcRI)," Nucleic Acids Research. 1988, vol. 16. No. 24; p. 11824.

Peltz, GA et al. "Human FcγRIII: Cloning, Expression, and Identification of the Chromosomal Locus of Two Fc Receptors for IgG," Proceedings of the National Academy of Sciences of the United States of America, Immunology. Feb. 1989, vol. 86. pp. 1013-1017.

* cited by examiner

CD64-CD16 Chimeric Receptor DNA (Domain-based construction)

CTTGGAGACAACATGTGGTTCTTGACAACTCTGCTCCTTTGGGTTCCAGTTGATGGGCAAGTGGACACCACAAAGGCAGTGATCACTTTGCAGCCTCCATG
GGTCAGCGTGTTCCAAGAGGAAACCGTAACCTTGCATTGTGAGGTGCTCCATCTGCCTGGGAGCAGCTCTACACAGTGGTTTCTCAATGGCACAGCCACT
CAGACCTCGACCCCCAGCTACAGAATCACCTCTGCCAGTGTCAATGACAGTGGTGAATACAGGTGCCAGAGAGGTCTCTCAGGGCGAAGTGACCCCATAC
AGCTGGAAATCCACAGAGGCTGGCTACTACTGCAGGTCTCCAGCAGAGTCTTCACGGAAGGAGAACCTCTGGCCTTGAGGTGTCATGCGTGGAAGGATA
AGCTGGTGTACAATGTGCTTTACTATCGAAATGGCAAAGCCTTTAAGTTTTTCCACTGGAATTCTAACCTCACCATTCTGAAAACCAACATAAGTCACAATGG
CACCTACCATTGCTCAGGCATGGGAAAGCATCGCTACACATCAGCAGGAATATCTGTCACTGTGAAAGAGCTATTTCCAGCTCCAGTGCTGAATGCATCTGT
GACATCCCCACTCCTGGAGGGGAATCTGGTCACCCTGAGCTGTGAAACAAAGTTGCTCTTGCAGAGGCCTGGTTTGCAGCTTTACTTCTCCTTCTACATGG
GCAGCAAGACCCTGCGAGGCAGGAACACATCCTCTGAATACCAAATACTAACTGCTAGAAGAGAAGACTCTGGGTTATACTGGTGCGAGGCTGCCACAGA
GGATGGAAATGTCCTTAAGCGCAGCCCTGAGTTGGAGCTTCAAGTGCTTGGCCTCCAGTTACCAACTCCTGTCTGGTTTCAT-
TACCAAGTCTCTTTCTGCTTGGTGATGGTACTCCTTTTTGCAGTGGACACAGGACTATATTTCTCTGTGAAGACAAACATTCGAAGCTCAACAAGAGACTGG
AAGGACCATAAATTTAAATGGAGAAAGGACCCTCAAGACAAA

Protein sequence (340 a.a.)

MWFLTTLLLWVPVDGQVDTTKAVITLQPPWVSVFQEETVTLHCEVLHLPGSSSTQWFLNGTATQTSTPSYRITSASVNDSGEYRCQRGLSGRSDPIQLEIHRGW
LLLQVSSRVFTEGEPLALRCHAWKDKLVYNVLYYRNGKAFKFFHWNSNLTILKTNISHNGTYHCSGMGKHRYTSAGISVTVKELFPAPVLNASVTSPLLEGNLVTL
SCETKLLLQRPGLQLYFSFYMGSKTLRGRNTSSEYQILTARREDSGLYWCEAATEDGNVLKRSPELELQVLGLQLPTPVWFHYQVSFCLVMVLLFAVDTGLYFSVKT
NIRSSTRDWKDHKFKWRKDPQDK

Figure 10

CD64-CD16 Chimeric Receptor DNA (Exon-based construction)

CTTGGAGACAACATGTGGTTCTTGACAACTCTGCTCCTTTGGGTTCCAGTTGATGGGCAAGTGGACACCACAAAGGCAGTGATCACTTTGCAGCCTCCATG
GGTCAGCGTGTTCCAAGAGGAAACCGTAACCTTGCATTGTGAGGTGCTCCATCTGCCTGGGAGCAGCTCTACACAGTGGTTTCTCAATGGCACAGCCACT
CAGACCTCGACCCCCAGCTACAGAATCACCTCTGCCAGTGTCAATGACAGTGGTGAATACAGGTGCCAGAGAGGTCTCTCAGGGCGAAGTGACCCCATAC
AGCTGGAAATCCACAGAGGCTGGCTACTACTGCAGGTCTCCAGCAGAGTCTTCACGGAAGGAGAACCTCTGGCCTTGAGGTGTCATGCGTGGAAGGATA
AGCTGGTGTACAATGTGCTTTACTATCGAAATGGCAAAGCCTTTAAGTTTTTCCACTGGAATTCTAACCTCACCATTCTGAAAACCAACATAAGTCACAATGG
CACCTACCATTGCTCAGGCATGGGAAAGCATCGCTACACATCAGCAGGAATATCTGTCACTGTGAAAGAGCTATTTCCAGCTCCAGTGCTGAATGCATCTGT
GACATCCCCACTCCTGGAGGGGAATCTGGTCACCCTGAGCTGTGAAACAAAGTTGCTCTTGCAGAGGCCTGGTTTGCAGCTTTACTTCTCCTTCTACATGG
GCAGCAAGACCCTGCGAGGCAGGAACACATCCTCTGAATACCAAATACTAACTGCTAGAAGAGAAGACTCTGGGTTATACTGGTGCGAGGCTGCCACAGA
GGATGGAAATGTCCTTAAGCGCAGCCCTGAGTTGGAGCTTCAAGTGCTTG-
GTTTGGCAGTGTCAACCATCTCATCATTCTTTCCACCTGGGTACCAAGTCTCTTTCTGCTTGGTGATGGTACTCCTTTTTGCAGTGGACACAGGACTATATTTC
TCTGTGAAGACAAACATTCGAAGCTCAACAAGAGACTGGAAGGACCATAAATTTAAATGGAGAAAGGACCCTCAAGACAAA

Protein seq (343 a.a.)

MWFLTTLLLWVPVDGQVDTTKAVITLQPPWVSVFQEETVTLHCEVLHLPGSSSTQWFLNGTATQTSTPSYRITSASVNDSGEYRCQRGLSGRSDPIQLEIHRG
WLLLQVSSRVFTEGEPLALRCHAWKDKLVYNVLYYRNGKAFKFFHWNSNLTILKTNISHNGTYHCSGMGKHRYTSAGISVTVKELFPAPVLNASVTSPLLEGNL
VTLSCETKLLLQRPGLQLYFSFYMGSKTLRGRNTSSEYQILTARREDSGLYWCEAATEDGNVLKRSPELELQVLGLAVSTISSFFPPGYQVSFCLVMVLLFAVDTGL
YFSVKTNIRSSTRDWKDHKFKWRKDPQDK

Figure 11

Mod4 DNA (CD28-CD134-CD137-CD3z)

AGGAGTAAGAGGAGCAGGCTCCTGCACAGTGACTACATGAACATGACTCCCCGCCGCCCCGGGCCCACCCGCAAGCATTACCAGCCCTATGCCCCA
CCACGCGACTTCGCAGCCTATCGCTCCggatctCGGAGGGACCAGAGGCTGCCCCCCGATGCCCACAAGCCCCCTGGGGGAGGCAGTTTCCGGACC
CCCATCCAAGAGGAGCAGGCCGACGCCCACTCCACCCTGGCCAAGATCggatctCGTTTCTCTGTTAAACGGGGCAGAAAGAAACTCCTGTATATATT
CAAACAACCATTTATGAGACCAGTACAAACTACTCAAGAGGAAGATGGCTGTAGCTGCCGATTTCCAGAAGAAGAAGAAGGAGGATGTGAACTGg
gatctAGAGTGAAGTTCAGCAGGAGCGCAGACGCCCCCGCGTACCAGCAGGGCCAGAACCAGCTCTATAACGAGCTCAATCTAGGACGAAGAGAG
GAGTACGATGTTTTGGACAAGAGACGTGGCCGGGACCCTGAGATGGGGGGAAAGCCGCAGAGAAGGAAGAACCCTCAGGAAGGCCTGTACAAT
GAACTGCAGAAAGATAAGATGGCGGAGGCCTACAGTGAGATTGGGATGAAAGGCGAGCGCCGGAGGGGCAAGGGGCACGATGGCCTTTACCAG
GGTCTCAGTACAGCCACCAAGGACACCTACGACGCCCTTCACATGCAGGCCCTGCCCCCTCGCTAA

Mod4 Protein seq (243 a.a.)

RSKRSRLLHSDYMNMTPRRPGPTRKHYQPYAPPRDFAAYRSGSRRDQRLPPDAHKPPGGGSFRTPIQEEQADAHSTLAKIGSRFSVKRGRKKLLYIFKQP
FMRPVQTTQEEDGCSCRFPEEEEGGCELGSRVKFSRSADAPAYQQGQNQLYNELNLGRREEYDVLDKRRGRDPEMGGKPQRRKNPQEGLYNELQKDK
MAEAYSEIGMKGERRRGKGHDGLYQGLSTATKDTYDALHMQALPPR

Figure 12

64-16D-M4G DNA
ATGTGGTTCTTGACAACTCTGCTCCTTTGGGTTCCAGTTGATGGGCAAGTGGACACCACAAAGGCAGTGATCACTTTGCAGCCTCCATGGGTCA
GCGTGTTCCAAGAGGAAACCGTAACCTTGCATTGTGAGGTGCTCCATCTGCCTGGGAGCAGCTCTACACAGTGGTTTCTCAATGGCACAGCCAC
TCAGACCTCGACCCCCAGCTACAGAATCACCTCTGCCAGTGTCAATGACAGTGGTGAATACAGGTGCCAGAGAGGTCTCTCAGGGCGAAGTGA
CCCCATACAGCTGGAAATCCACAGAGGCTGGCTACTACTGCAGGTCTCCAGCAGAGTCTTCACGGAAGGAGAACCTCTGGCCTTGAGGTGTCA
TGCGTGGAAGGATAAGCTGGTGTACAATGTGCTTTACTATCGAAATGGCAAAGCCTTTAAGTTTTTCCACTGGAATTCTAACCTCACCATTCTGAA
AACCAACATAAGTCACAATGGCACCTACCATTGCTCAGGCATGGGAAAGCATCGCTACACATCAGCAGGAATATCTGTCACTGTGAAAGAGCTAT
TTCCAGCTCCAGTGCTGAATGCATCTGTGACATCCCCACTCCTGGAGGGGAATCTGGTCACCCTGAGCTGTGAAACAAAGTTGCTCTTGCAGAG
GCCTGGTTTGCAGCTTTACTTCTCCTTCTACATGGGCAGCAAGACCCTGCGAGGCAGGAACACATCCTCTGAATACCAAATACTAACTGCTAGAA
GAGAAGACTCTGGGTTATACTGGTGCGAGGCTGCCACAGAGGATGGAAATGTCCTTAAGCGCAGCCCTGAGTTGGAGCTTCAAGTGCTTGGCC
TCCAGTTACCAACTCCTGTCTGGTTTCATTACCAAGTCTCTTTCTGCTTGGTGATGGTACTCCTTTTTGCAGTGGACACAGGACTATATTTCTCTGT
GAAGACAAACATTCGAAGCTCAACAAGAGACTGGAAGGACCATAAATTTAAATGGAGAAAGGACCCTCAAGACAAAggatctAGGAGTAAGAG
GAGCAGGggCggGCACAGTGACTACATGAACATGACTCCCCGCCGCCCCGGGCCCACCCGCAAGCATTACCAGCCCTATGCCCCACCACGCGAC
TTCGCAGCCTATCGCTCCggatctCGGAGGGACCAGAGGCTGCCCCCCGATGCCCACAAGCCCCTGGGGGAGGCAGTTTCCGGACCCCCATCC
AAGAGGAGCAGGCCGACGCCCACTCCACCCTGGCCAAGATCggatctCGTTTCTCTGTTAAACGGGGCAGAAAGAAACTCCTGTATATATTCAAA
CAACCATTTATGAGACCAGTACAAACTACTCAAGAGGAAGATGGCTGTAGCTGCCGATTTCCAGAAGAAGAAGAAGGAGGATGTGAACTGggat
ctAGAGTGAAGTTCAGCAGGAGCGCAGACGCCCCCGCGTACCAGCAGGGCCAGAACCAGCTCTATAACGAGCTCAATCTAGGACGAAGAGAG
GAGTACGATGTTTTGGACAAGAGACGTGGCCGGGACCCTGAGATGGGGGGAAAGCCGCAGAGAAGGAAGAACCCTCAGGAAGGCCTGTAC
AATGAACTGCAGAAAGATAAGATGGCGGAGGCCTACAGTGAGATTGGGATGAAAGGCGAGCGCCGGAGGGGCAAGGGGCACGATGGCCTTT
ACCAGGGTCTCAGTACAGCCACCAAGGACACCTACGACGCCCTTCACATGCAGGCCCTGCCCCCTCGCTAA

64-16D-M4G Protein (585 a.a.)
MWFLTTLLLWVPVDGQVDTTKAVITLQPPWVSVFQEETVTLHCEVLHLPGSSSTQWFLNGTATQTSTPSYRITSASVNDSGEYRCQRGLSGRSDPIQ
LEIHRGWLLLQVSSRVFTEGEPLALRCHAWKDKLVYNVLYYRNGKAFKFFHWNSNLTILKTNISHNGTYHCSGMGKHRYTSAGISVTVKELFPAPVL
NASVTSPLLEGNLVTLSCETKLLLQRPGLQLYFSFYMGSKTLRGRNTSSEYQILTARREDSGLYWCEAATEDGNVLKRSPELELQVLGLQLPTPVWFHY
QVSFCLVMVLLFAVDTGLYFSVKTNIRSSTRDWKDHKFKWRKDPQDKGSRSKRSRGGHSDYMNMTPRRPGPTRKHYQPYAPPRDFAAYRSGSRRD
QRLPPDAHKPPGGGSFRTPIQEEQADAHSTLAKIGSRFSVKRGRKKLLYIFKQPFMRPVQTTQEEDGCSCRFPEEEEGGCELGSRVKFSRSADAPAYQ
QGQNQLYNELNLGRREEYDVLDKRRGRDPEMGGKPQRRKNPQEGLYNELQKDKMAEAYSEIGMKGERRRGKGHDGLYQGLSTATKDTYDALHM
QALPPR

Figure 13

64-16E-M4G DNA
ATGTGGTTCTTGACAACTCTGCTCCTTTGGGTTCCAGTTGATGGGCAAGTGGACACCACAAAGGCAGTGATCACTTTGCAGCCTCCATGGGTCAGC
GTGTTCCAAGAGGAAACCGTAACCTTGCATTGTGAGGTGCTCCATCTGCCTGGGAGCAGCTCTACACAGTGGTTTCTCAATGGCACAGCCACTCA
GACCTCGACCCCCAGCTACAGAATCACCTCTGCCAGTGTCAATGACAGTGGTGAATACAGGTGCCAGAGAGGTCTCTCAGGGCGAAGTGACCCCA
TACAGCTGGAAATCCACAGAGGCTGGCTACTACTGCAGGTCTCCAGCAGAGTCTTCACGGAAGGAGAACCTCTGGCCTTGAGGTGTCATGCGTGG
AAGGATAAGCTGGTGTACAATGTGCTTTACTATCGAAATGGCAAAGCCTTTAAGTTTTTCCACTGGAATTCTAACCTCACCATTCTGAAAACCAACAT
AAGTCACAATGGCACCTACCATTGCTCAGGCATGGGAAAGCATCGCTACACATCAGCAGGAATATCTGTCACTGTGAAAGAGCTATTTCCAGCTCC
AGTGCTGAATGCATCTGTGACATCCCCACTCCTGGAGGGGAATCTGGTCACCCTGAGCTGTGAAACAAAGTTGCTCTTGCAGAGGCCTGGTTTGC
AGCTTTACTTCTCCTTCTACATGGGCAGCAAGACCCTGCGAGGCAGGAACACATCCTCTGAATACCAAATACTAACTGCTAGAAGAGAAGACTCTG
GGTTATACTGGTGCGAGGCTGCCACAGAGGATGGAAATGTCCTTAAGCGCAGCCCTGAGTTGGAGCTTCAAGTGCTTGGTTTGGCAGTGTCAACC
ATCTCATCATTCTTTCCACCTGGGTACCAAGTCTCTTTCTGCTTGGTGATGGTACTCCTTTTTGCAGTGGACACAGGACTATATTTCTCTGTGAAGAC
AAACATTCGAAGCTCAACAAGAGACTGGAAGGACCATAAATTTAAATGGAGAAAGGACCCTCAAGACAAAggatctAGGAGTAAGAGGAGCAGGg
gCggGCACAGTGACTACATGAACATGACTCCCCGCCGCCCCGGGCCCACCCGCAAGCATTACCAGCCCTATGCCCCACCACGCGACTTCGCAGCCT
ATCGCTCCggatctCGGAGGGACCAGAGGCTGCCCCCCGATGCCCACAAGCCCCTGGGGGAGGCAGTTTCCGGACCCCCATCCAAGAGGAGCAG
GCCGACGCCCACTCCACCCTGGCCAAGATCggatctCGTTTCTCTGTTAAACGGGGCAGAAAGAAACTCCTGTATATATTCAAACAACCATTTATGAG
ACCAGTACAAACTACTCAAGAGGAAGATGGCTGTAGCTGCCGATTTCCAGAAGAAGAAGAAGGAGGATGTGAACTGggatctAGAGTGAAGTTCA
GCAGGAGCGCAGACGCCCCCGCGTACCAGCAGGGCCAGAACCAGCTCTATAACGAGCTCAATCTAGGACGAAGAGAGGAGTACGATGTTTTGGA
CAAGAGACGTGGCCGGGACCCTGAGATGGGGGGAAAGCCGCAGAGAAGGAAGAACCCTCAGGAAGGCCTGTACAATGAACTGCAGAAAGATA
AGATGGCGGAGGCCTACAGTGAGATTGGGATGAAAGGCGAGCGCCGGAGGGGCAAGGGGCACGATGGCCTTTACCAGGGTCTCAGTACAGCC
ACCAAGGACACCTACGACGCCCTTCACATGCAGGCCCTGCCCCCTCGCTAA

64-16E-M4G Protein (588 a.a.)
MWFLTTLLLWVPVDGQVDTTKAVITLQPPWVSVFQEETVTLHCEVLHLPGSSSTQWFLNGTATQTSTPSYRITSASVNDSGEYRCQRGLSGRSDPIQ
LEIHRGWLLLQVSSRVFTEGEPLALRCHAWKDKLVYNVLYYRNGKAFKFFHWNSNLTILKTNISHNGTYHCSGMGKHRYTSAGISVTVKELFPAPVLN
ASVTSPLLEGNLVTLSCETKLLLQRPGLQLYFSFYMGSKTLRGRNTSSEYQILTARREDSGLYWCEAATEDGNVLKRSPELELQVLGLAVSTISSFFPPGY
QVSFCLVMVLLFAVDTGLYFSVKTNIRSSTRDWKDHKFKWRKDPQDKGSRSKRSRGGHSDYMNMTPRRPGPTRKHYQPYAPPRDFAAYRSGSRRD
QRLPPDAHKPPGGGSFRTPIQEEQADAHSTLAKIGSRFSVKRGRKKLLYIFKQPFMRPVQTTQEEDGCSCRFPEEEEGGCELGSRVKFSRSADAPAYQ
QGQNQLYNELNLGRREEYDVLDKRRGRDPEMGGKPQRRKNPQEGLYNELQKDKMAEAYSEIGMKGERRRGKGHDGLYQGLSTATKDTYDALHM
QALPPR

Figure 14

SYNTHETIC BIOLOGY-BASED ADCC TECHNOLOGY

CROSS-REFERENCE TO RELATED APPLICATIONS

This application claims priority to and the benefit of co-pending U.S. provisional patent application Ser. No. 61/925,217, filed on Jan. 8, 2014 and bearing the same title, which application is incorporated herein by reference in its entirety.

TECHNICAL FIELD

The invention relates to synthetic biology products and processes that can be used to enhance an immune effector cell's ability to mediate antibody-dependent cellular cytotoxicity (ADCC) or to enable cells to mediate ADCC as well as methods of using them in the treatment and prevention of cancer, infectious diseases, inflammatory and autoimmune diseases and other diseases.

BACKGROUND OF INVENTION

Mammals, especially higher vertebrates including human, have developed highly complex immune systems that use multiple mechanisms and effectors to detect, destroy, or at least contain foreign pathogens as well as diseased or stressed autologous cells. These diseased cells may have been infected by virus or bacteria, or have become cancerous.

One of the mechanisms for the immune system to recognize and eliminate diseased host cells and invading intracellular microorganisms (e.g., viruses, bacteria or parasites) is through cell-mediated cytotoxicity, which can be carried out by a number of leukocytes and proteins. These potentially cytotoxic effectors include: from the lymphoid lineage—Natural Killer (NK) cells and cytotoxic T lymphocytes (CTLs); and from the myeloid lineage—macrophages, neutrophils and eosinophils.

An important way for the immune system to unleash cell-mediated cytotoxicity relies on antibodies. Over the past decade, monoclonal antibodies (mAbs) that target tumor-specific cell-surface proteins have become a popular therapeutic approach against cancers. Several mAbs have entered routine clinical practice including rituximab (Rituxan, Mabthera), trastuzumab (Herceptin) and cetuximab (Erbitux). The popularity of mAbs is a result of their bifunctional nature. One end of an antibody (Fab) can be made exquisitely specific to a particular tumor protein without altering the other end (Fc) which recruits a variety of effector cells and proteins that kill the tumor cell.

Specifically, after recognizing and binding antigens on the surface of a target cell first, antibodies act as an adapter and proceed to activate the cytotoxic capability of immune effector cells through a second binding with certain receptors on those effector cells. This is called the antibody-dependent cellular cytotoxicity (ADCC). For example, in the context of innate immunity against cancer, ADCC is primarily mediated by natural killer (NK) cells (and, to a lesser extent, neutrophils, monocytes and macrophages) that express a relatively low-affinity Fc receptor (FcγRIIIa, also known as CD16a) that is only activated upon binding the Fc (constant) portions of antibodies coating a multivalent antigen on a target diseased cell (e.g., a tumor cell). This binding triggers the release of cytotoxic granules like perforin and granzyme (as well as many cytokines including IFN-γ), leading to the lysis of the target cell. The importance of the ADCC response has been shown both in vitro as well as in animal studies. Moreover, several clinical studies have shown that patients carrying a lower affinity variant of CD16 (F158) have worse clinical outcomes.

However, ADCC efficacy, as primarily mediated by endogenous natural killer (NK) cells, is limited in the body due to a number of physiological as well as pathological reasons as explained below (to the extent that endogenous Cytotoxic T lymphocytes participate in tumor clearance at all, their efficacy has also been found to be very limited and lacking).

First, most cells involved in the ADCC response such as macrophages and neutrophils do not tend to proliferate when they are activated. NK cells also have limited proliferation potential in response to activation, and they also rapidly die off. Therefore, natural ADCC response in the body risks being overwhelmed by disease progression (e.g., viral infection, cancer) even if the ADCC effectors recognize antibodies coating diseased cells.

Second, many of the ADCC effector cells also express inhibitory receptors that dampen their immune responsiveness, thereby instituting a system of balances and checks. These receptors include inhibitory KIRs (killer immunoglobulin-like receptors) for $CD56^{low}$ NK cells, FcγRIIb on monocytes and B cells, and CTLA-4 (CD152) and PD-1 (Programmed-Death-1, CD279) for T cells. Cancer cells and viruses counteract body's ADCC-based defense system by abnormally amplifying such inhibitory pathways.

Third, the main Fc receptor on ADCC effector cells, FcγRIIIa, has a relatively low affinity ($Kd \approx 10^{-6}$ M) for antibodies—even the V158 variant of the receptor has only a two-fold higher affinity compared to the ineffective F158 form of the receptor. This is one mechanism through which cancer cells become resistant to some therapeutic monoclonal antibodies (mAbs) once the density of the cell surface targets fall below a certain level.

In view of its natural limitations in proliferation and affinity as well as further depression through inhibitory Fc receptors in the setting of a disease, such as cancer or other diseases, the body's ADCC function has great potential that is never fully realized. Therefore, synthetic biology represents a novel and highly desirable approach to unleash the full potential of ADCC activity in the prevention and treatment of human diseases.

BRIEF SUMMARY OF THE INVENTION

The present invention ushers in new approaches to improve the immune system's defense against cancer, infections and other diseases. Using tools from synthetic biology and recombinant technology, the present invention aims to design and build an ADCC Enhancer or enhancing system that will greatly improve the effectiveness of ADCC response against many kinds of diseases including cancers. In one aspect, the present invention improves the detection sensitivity and efficiency of the ADCC defense system by enhancing its binding affinity at the "sensor" part of the system without compromising the specificity. In another aspect, the present invention improves the "effector" part of the system by enhancing the proliferation potential of the cytotoxic effector cells. In preferred embodiments, more than one of the above aspects are combined. Other embodiments of the present invention, however, may only reflect one of the afore-mentioned inventive aspects.

The ADCC Enhancer of the present invention can be used either in combination with an antibody therapy or by itself to target diseased cells recognized or bound by a naturally-occurring antibody or manmade antibody administered for a therapeutic purpose.

In the first aspect, which focuses on the "sensor" part of the ADCC enhancing system, the present invention sets out to build an ectodomain, or extracellular domain, with higher affinity for an antibody than that of the wildtype human CD16 (e.g., the most common form of human CD16, the F158 variant). This results in a high-affinity transmembrane Fc receptor and its extracellular portion can be based on the ectodomain of an existing Fc receptor. The "chimeric" or "fusion" receptor, in part or in whole, may be borrowed from another macromolecule in the immune system or engineered anew. Having a high-affinity Fc receptor enables an immune effector cell to efficiently bind the same Fc fragment common to different antibodies, which in turn, target a wide variety of cell surface antigens and thereby a wide variety of diseases and indications. This is a great advantage compared to antigen-dependent immunotherapies where each time, a different antibody needs to be built against each specific antigen, a process that is costly in time and other resources.

In the second aspect, where the focus moves to the "effector" part of the ADCC system, the present invention incorporates module(s) that, once expressed, can promote amplification of the ADCC effector cells.

Accordingly, in an embodiment, the present invention provides a genetic construct that encodes: a transmembrane chimeric receptor comprising an ectodomain having a higher binding affinity to the Fc of an antibody than that of the F158 variant of human CD16, a transmembrane domain, and an endodomain for mediating ADCC activation and amplification.

The genetic construct of the invention can include a DNA or RNA molecule. The construct may include substantially the EC3 exon of, e.g., human, CD64 or, in addition, substantially the EC1 and EC2 exons of (human) CD64. Alternatively, the genetic construct of the invention includes an RNA that translates to an ectodomain comprising substantially the ectodomain of CD64. In a feature, the ectodomain is selected based on boundaries of exons or domains in CD64. Preferably, the ectodomain has a higher affinity for Fc than the V158 variant of human CD16. In another feature, the transmembrane chimeric receptor is expressed as a fusion protein. Also, the endodomain may include amplification module(s), which may be selected from the group consisting of portions or all of intracellular domains of CD3ζ, of CD28, of CD134, of CD137, of CD27, of CD79a, of CD79b, of CD40 and of the GM-CSF receptor.

In a further embodiment, the present invention provides a transmembrane chimeric receptor that translates from the above genetic construct. In one feature, the ectodomain of the receptor of the invention comprises substantially the immunoglobulin-like fold in the ectodomain of CD64 that is absent from CD16, or, substantially the ectodomain of CD64. In one feature, the transmembrane domain comprises substantially the transmembrane domain of CD16. The receptor may further include an ADCC amplification module that enhances the survival and proliferation of a host immune effector cell. The amplification module may be selected from the group consisting of portions or all of intracellular domains of CD3ζ, of CD28, of CD134, of CD137, of CD27, of CD79a, of CD79b, of CD40 and of the GM-CSF receptor.

In another embodiment, the present invention provides an immune effector cell infected or transfected ex vivo with the genetic construct or the protein of the invention. The immune effector cell can be, e.g., a cytotoxic T lymphocyte, a natural killer cell, an eosinophil, a macrophage, a neutrophil, a basophil, a monocyte, a B cell, and other cells that express or are engineered to express cytotoxic factors.

In yet another embodiment, the present invention provides a pharmaceutical composition that includes the genetic construct, the protein, or the immune effector cell of the invention, and a pharmaceutically acceptable excipient.

In a further embodiment, the present invention provides a method of treating a subject in need thereof for a condition therapeutically or prophylactically, where the method includes administering to said subject a therapeutically or prophylactically effective amount of the pharmaceutical composition of the invention. In one feature, the method further includes administering a therapeutic antibody against at least one cell-surface antigen indicative of said condition. The immune effector cell may be autologous to said subject, and the condition selected from the group consisting of a cancer, an inflammatory disease, an autoimmune disease, transplant rejection and an infection. In a feature, the pharmaceutical composition of the invention is administered as a vaccine against said condition.

In a yet another embodiment, the present invention provides a method of treating a subject in need thereof for a condition therapeutically or prophylactically by (a) priming dendritic cells isolated from said subject with a source of antigen; (b) infusing said primed dendritic cells back into said subject; (c) administering to said subject a therapeutically or prophylactically effective amount of the pharmaceutical composition of the present invention. The source of the antigen may be autologous or foreign, and the condition may be selected from the group consisting of a cancer, an inflammatory disease, an autoimmune disease, transplant rejection and an infection.

BRIEF DESCRIPTION OF FIGURES

FIG. 10 lists a DNA sequence (SEQ ID NO:1) (top) that would translate into chimeric receptors according to embodiments of the invention where an extracellular region of human CD64 is fused to regions of human CD16 using a domain-based strategy (point of fusion marked by a dash). The corresponding protein sequence (SEQ ID NO:2) is listed in the bottom.

FIG. 11 lists a DNA sequence (SEQ ID NO:3) (top) that would translate into chimeric receptors according to embodiments of the invention where an extracellular region of human CD64 is fused to regions of human CD16 using an exon-based strategy (point of fusion marked by a dash). The corresponding protein sequence (SEQ ID NO:4) is listed in the bottom.

FIG. 12 lists a DNA sequence (SEQ ID NO:5) of an intracellular region of a chimeric receptor according to an embodiment of the invention where the region consists of amplification modules from human CD28, human CD134, human CD137 and human CD3ζ. The corresponding protein sequence (SEQ ID NO:6) is listed in the bottom. Spacer sequences are written in small letters.

FIG. 13 lists a DNA sequence (SEQ ID NO:7) (top) that would translate into chimeric receptors according to embodiments of the invention where an extracellular region of human CD64 is fused to regions of human CD16 using an domain-based strategy is further fused to amplification modules depicted in FIG. 13. The corresponding protein sequence (SEQ ID NO:8) is listed in the bottom. Spacer sequences are written in small letters.

FIG. 14 lists a DNA sequence (SEQ ID NO:9) (top) that would translate into chimeric receptors according to embodiments of the invention where an extracellular region of human CD64 is fused to regions of human CD16 using an exon-based strategy is further fused to amplification modules depicted in FIG. 13. The corresponding protein sequence (SEQ ID NO:10) is listed in the bottom. Spacer and mutation sequences are written in small letters.

DETAILED DESCRIPTION OF INVENTION

I. Definition

Figure 1:
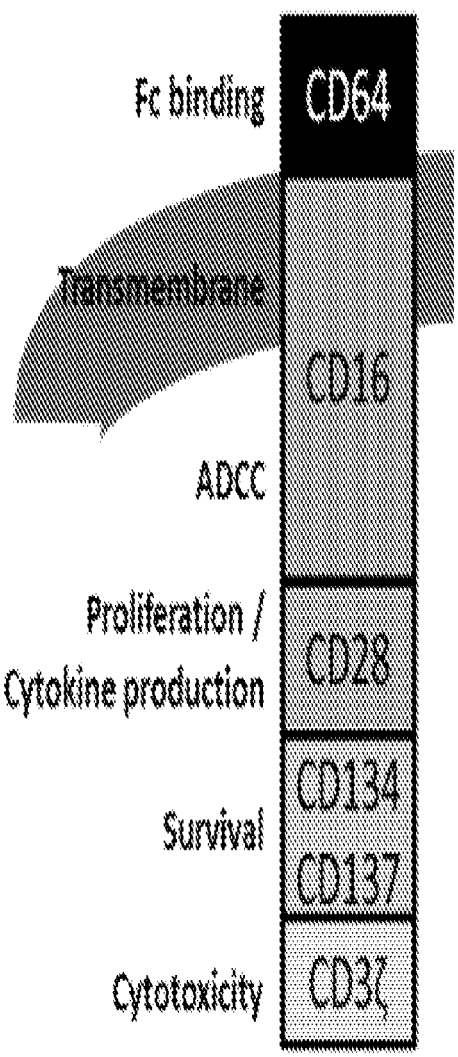
FIG. 1 schematically depicts the embodiment of the chimeric antibody-receptor according to the present invention. The chimeric receptor has an extracellular domain with relatively high affinity for the Fc portion of antibodies as well as an intracellular signaling domain that has relatively high proliferation-stimulating activity.

Unless otherwise noted, technical terms are used according to conventional usage. Definitions of common terms in molecular biology may be found, for example, in Benjamin Lewin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar technical references.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5 to 10% of the recited value) that one of ordinary skill in the art would consider equivalent to the recited value (e.g., having the same function or result). In some instances, the term "about" may include numerical values that are rounded to the nearest significant figure.

CD16 is expressed as two distinct forms, CD16a and CD16b, which are products of two different yet highly homologous genes. CD16a is a polypeptide-anchored transmembrane protein while CD16b is a glycosylphosphatidylinositol-anchored protein. As used herein, CD16 refers to both forms of the protein, unless inappropriate as would be apparent to one skilled artisan.

The ADCC Enhancer of the present invention can be incorporated in any immune effector with cytotoxic capability, including but are not limited to: T cells including cytotoxic T lymphocytes (CTLs) and helper T cells, NK cells (large granular lymphocytes), eosinophils, macrophages, neutrophils, basophils, monocytes, and B cells. Effector cells of the present invention may be autologous, syngeneic or allogeneic, with the selection dependent upon the disease to be treated and means available.

II. Composition

The present invention develops an ADCC enhancing system that has one or more of the following distinguishing features: (a) a genetic material that encodes a chimeric receptor having improved affinity for the Fc fragment of antibodies bound to the surface of a target cell; (b) a genetic material that encodes protein and/or RNA module(s) that enhance proliferation and survival of ADCC effector cells upon engagement with a targeted diseased cell that is tagged by a naturally occurring or therapeutic antibody; (c) a genetic material that encodes protein and/or RNA module(s) that amplify the efficiency of ADCC response. Towards this end, a genetic construct that encodes such component(s) are introduced, as the ADCC-enhancing system, either in vivo or ex vivo, into the cells of a host, e.g., a patient subject:

A chimeric receptor that contains a high-affinity, Fc-binding ectodomain fused to a transmembrane and an intracellular domain that activates ADCC and leads to effector proliferation (FIG. 1);

(1) Chimeric Receptor

Depending on the effector, the chimeric receptor can include portions of natural constituents of the effector, for instance, parts or all of the ectodomain, transmembrane domain and/or the intracellular domain of a native receptor. The host contemplated by the present invention is high vertebrate, preferably mammalian, further preferably human. The chimeric receptor of the present invention includes an extracellular domain (ectodomain), a transmembrane domain, and an intracellular domain (cytoplasmic domain or endodomain).

(1)(a) Ectodomain

Figure 2:
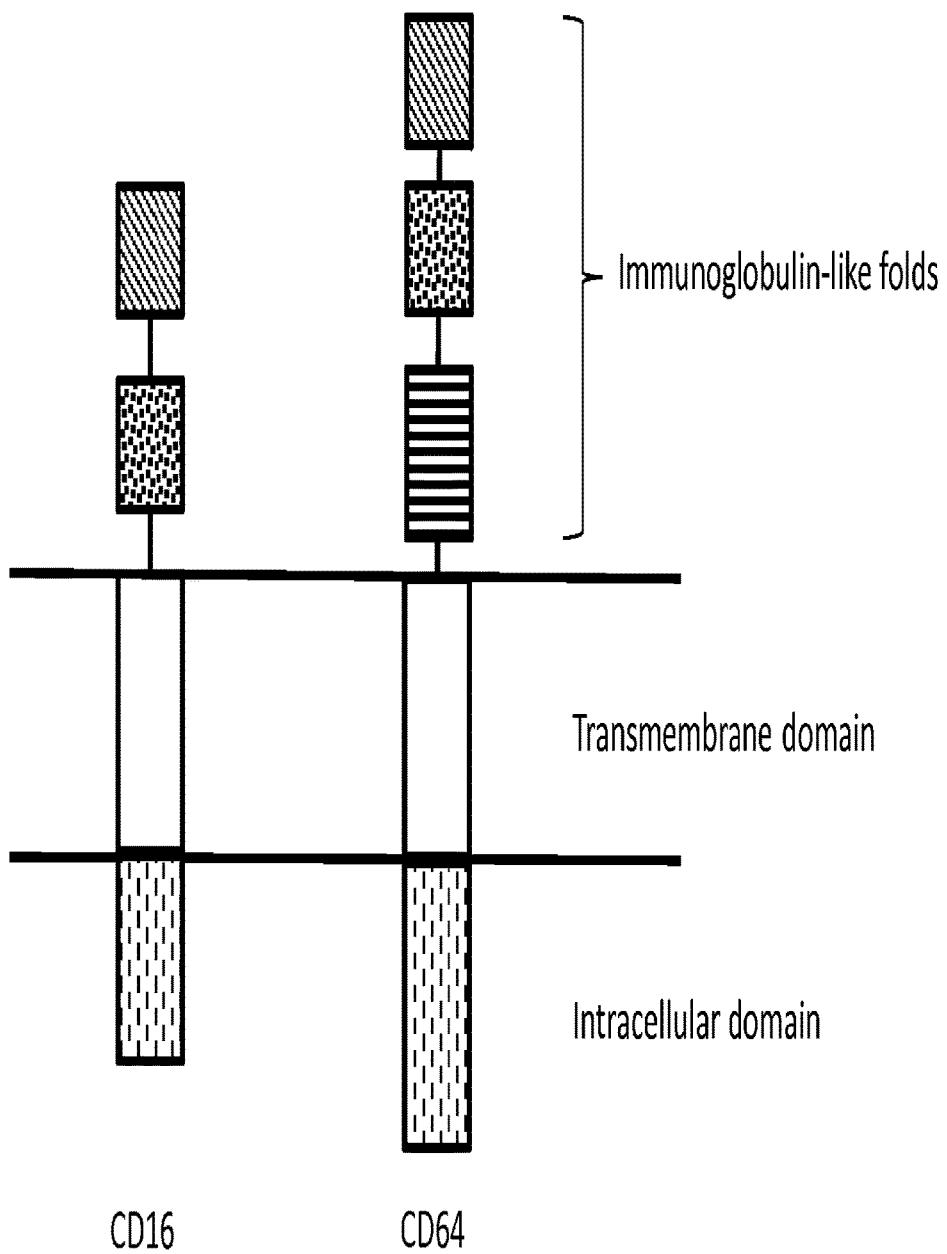
FIG. 2 schematically compares the protein domain structures of CD16 and CD64 where the extracellular domains of CD16 and CD64 consist of two and three immunoglobulin folds, respectively. Similar shadings represent homologous folds.

Referring to FIG. 1, in one embodiment (left), the chimeric receptor of the present invention incorporates parts or all of the ectodomain of CD64 (FcγRI). While both CD64 and CD16 bind to the Fc region of antibodies, the former has about a 100- to a 1000-fold higher affinity. FcγRI (CD64), the high-affinity Fc receptor (Kd≈$10^{-9}$ M for IgG1 and IgG3), is present on all cells of the mononuclear phagocyte lineage (e.g., macrophages and neutrophils), and is responsible for antibody-mediated phagocytosis and mediator release. As shown in FIG. 2, FcγRI includes a glycoprotein a chain whose extracellular domain is comprised of three immunoglobulin domains that are responsible for binding to antibodies, and the presence of all three have been shown to be critical for high affinity interaction with antibodies. In contrast, CD16's ectodomain only has two immunoglobulin-like domains. The presence of the extra immunoglobulin-like fold in CD64 may be a strong determinant of its high Fc affinity. To that extent, the present invention also contemplates inserting only this extra immunoglobulin-like fold in CD64 or a mutant version of it into CD16's ectodomain in order to construct a high-affinity receptor for antibodies.

According to the present embodiment, the ectodomain of CD64 (FcγRI) is fused to any suitable transmembrane and intracellular domains to generate a high-affinity Fc receptor that mediates ADCC. In a preferred embodiment, the ectodomain of human CD64 (FcγRI) is fused to parts of human CD16 (FcγRIII), e.g., both the transmembrane and intracellular domains of CD16, preferably, of CD16a (FcγRIIIa). Advantageously, with the ectodomain being native to the body, the chimeric receptor in this embodiment is syngeneic and, therefore, non-immunogenic.

As shown in FIG. 1, there may be additional modules in the intracellular domain of the chimeric receptor of the present invention. This could include one or more modules that can amplify the proliferation and expansion signal (e.g., CD28), one or more modules that promote the effector cell survival and prevent activation-induced apoptosis (e.g., CD134 and CD137), one or more modules that activate or boost signal transduction for proliferation and cytotoxicity (e.g., CD3ζ). Details of these amplificatory and stimulatory modules are further described in the following sections.

(1)(b) Transmembrane Domain

The transmembrane domain of the chimeric receptor of the present invention can be any suitable hydrophobic region that can span the cellular membrane, preferably in a stable fashion. In a preferred embodiment, the transmembrane domain is natural to its neighboring component of the intracellular domain. For example, as shown in FIG. 1, in an embodiment where the component or region of the intracellular domain that is closest to the membrane derives from CD16, the transmembrane domain is preferably the transmembrane domain of CD16.

(1)(c) Endodomain (1)(c)(i) Signaling for ADCC

Referring again to FIG. 1, in various embodiments of the present invention, the chimeric receptor includes one or more signaling modules for ADCC. CD16 is the natural antibody receptor that activates the effector cells responsible for most of the ADCC activities in our body, particularly the NK cells. Accordingly, in various embodiments, the endodomain of the chimeric receptor of the present invention includes parts or the entire intracellular domain of CD16, preferably, CD16a. Other modules such as CD3ζ, which share similar ITAM domains with CD16a, also may be included to contribute to the ADCC signaling. In some embodiments, CD3ζ may not be needed for ADCC signaling as long as the CD16a intracellular domain is expressed in tandem with other co-stimulatory modules or elements. Conversely, modules like CD3ζ might be able to replace the function of the intracellular domain of CD16, rendering it unnecessary.

(1)(c)(ii) Amplification Module

As shown in FIG. 1, the chimeric receptor of the present invention may include elements for amplifying the ADCC response. Depending on the effector cell, one or more amplification modules might be included in the chimeric receptor, serving varying functions. The following modules are described as non-limiting examples and for illustrative purposes.

In an embodiment, the endodomain of the chimeric receptor of the present invention includes parts or the entire intracellular domain of CD3ζ. A marker native to the T cell surface, CD3ζ has been shown to have stimulatory effect on lymphocyte (e.g., T cell) activation and proliferation, bringing about a much amplified cytotoxic T cell response.

In various embodiments, one or more additional costimulatory modules are added to the chimeric receptor of the invention so that the activation effect is sustained for a significantly longer time, thereby increasing the proliferation and expansion potential. An example is CD28's signaling domain, which has been shown to enhance the survival and proliferation of T lymphocytes when expressed with the TCRζ domain in an antigen-dependent receptor (Krause et al, J. Exp. Med. 188:619-26, 1998). Other optional modules that can be incorporated into the chimeric receptor of the present invention include the intracellular domain of members of the tumor necrosis factor receptor family such as CD134 (OX40), CD137 (4-1BB), CD27, for boosting the survival of the effector cells by preventing activation-induced apoptosis (see, e.g., Finney et al., *J Immunol.*, 2004, 172:104-13). Other intracellular domains that could aid in proliferation in some or multiple cell types are found in CD79a, CD79b, CD40, and the GM-CSF receptor.

(2) Cellular Expression

Using standard recombinant technologies, one or more of the expression cassettes for the chimeric receptor are constructed and cloned onto a vector, e.g., that of a plasmid, adenovirus-derived vectors, retrovirus, or lentivirus. The vector is transfected (or, transduced in the case of viral-mediated gene integration) into any type of immune effector cells. Retroviral transduction may be performed using known techniques, such as that of Johnson et al. (Blood 114, 535-46, 2009). Successful transfection and surface display of the chimeric receptor is confirmed using convention means, e.g., by flow cytometry.

In an embodiment, immune effector cells are extracted from whole blood from a human patient as peripheral blood mononucleated cells (PBMCs), which include lymphocytes (CD4+ T cells, CD8+ T cells, B cells and NK cells), monocytes, macrophages, and so on. Optionally, effector cells are further prepared by enriching selected subset(s) of PBMCs for practicing the invention. In a particular embodiment, B cells are removed from the cell mixture.

The ability of transduced cells to bind antibodies is revealed using flow cytometry. Cells' ability to bind antibody-coated cells, release cytokines, perform ADCC and proliferate is tested and confirmed ex vivo and in vivo using standard assays and models (e.g., mouse xenograft models) well known to one skilled in the art.

III. Therapeutics and Vaccines

Clinical implications of the ADCC Enhancer for cancer can be revealed using human cancer cells in conjunction with therapeutic antibodies. For example, Daudi cells are treated with (1) Rituximab (trade name Rituxan®) which targets CD20 implicated in lymphoma, autoimmune diseases and transplant rejection, resulting in effector cell activation, degranulation and proliferation, and (2) immune effector cells transduced with the ADCC Enhancer. Target cell killing is also observed. In vivo testing is performed using commercially available NOD.scid. IL2R$\gamma^{-/-}$ mice which have very low T and B cells and no NK cells. Alternatively, NOD.Scid mice which have very low T and B cells and reduced NK cells are used. These mice are engrafted with labeled Daudi cells and tumor growth is observed and measured using any suitable imaging technique. In mice receiving Rituximab and immune effector cells transduced with the ADCC Enhancer, sustained periods of tumor remission, regression, or long-term non-progression are observed.

In another example, SK-BR-3 or MCF-7 cells are treated with (1) immune effector cells transduced with the ADCC Enhancer and (2) Trastuzumab (trade name Herceptin®) which targets the HER2/neu implicated in breast cancers, resulting in effector cell activation, degranulation and proliferation. Target cell killing is also observed. In vivo anti-tumor potency of the ADCC Enhancer is observed in mice models similar to the example described immediately above.

The clinical use of the ADCC Enhancer in autoimmunity can be revealed using one of the well-established mouse models for this kind of diseases. For instance, antibody-mediated B cell deletion has been shown to prevent and even reverse type-1 diabetes in NOD mice. However, this effect is limited by the low affinity of the Fc receptors (Hu et al. *J Clin Invest.* 2007, 117(12):3857-67; Xiu et al. *J Immunol.* 2008, 180(5):2863-75). Control mice are compared with mice receiving either anti-CD19 or anti-CD20 antibodies alone or in combination with murine immune effector cells transduced with or otherwise expressing the ADCC Enhancer of the present invention. The mice receiving the ADCC Enhancer show delayed onset of disease or sustained reversal of symptoms.

Similar experiments can be performed in other mouse models where antibody-mediated depletion has been shown to impact diseases such as multiple sclerosis, or experimental autoimmune encephalomyelitis (Ban et al. *J Exp Med.* 2012, 209(5): 1001-10)), arthritis (Yanaba et al. *J Immunol.* 2007, 179(2): 1369-80), and so on.

The clinical use of the ADCC Enhancer in viral infections such as HIV infection can be revealed using well-established humanized mouse model where treatment with a combination of antibodies has been shown to control HIV replication (*Nature,* 2012, 492(7427): 118-22). Humanized mice are first generated by reconstituting NOD.RAG1$^{-/-}$. IL2R$\gamma^{-/-}$ mice with human fetal liver-derived CD34+ hematopoietic stem cells. These mice have a completely human immune system, can be infected by HIV and do not negatively react to human antibodies. Infected control mice are compared with mice receiving either neutralizing antibody cocktail alone or in combination with human immune effector cells transduced with the ADCC Enhancer of the present invention. The mice receiving the ADCC enhancer show sustained reduction in viremia and recovery of T cell numbers.

An alternate model system to test the clinical efficacy of the ADCC Enhancer is the simian-human immunodeficiency virus (SHIV)-infected infant rhesus macaque model where neutralizing antibodies have been shown to prevent rapid onset of the disease (Jaworski et al. *J Virol.* 2013, 87(19): 10447-59). Infected control macaques are compared with those receiving either neutralizing antibody cocktail alone or in combination with immune effector cells transduced with the ADCC Enhancer of the present invention. The macaques receiving the ADCC enhancer similarly show sustained reduction in viremia and recovery of T cell numbers.

DNA and RNA constructs that encode the ADCC Enhancing system of the present invention may be formulated for administration to a subject using techniques known to the skilled artisan. Formulations comprising DNA and RNA constructs that encode the ADCC Enhancing system may include pharmaceutically acceptable excipient(s). Excipients included in the formulations will have different purposes depending, for example, on the kind of gene construct or effector cells used, and the mode of administration. Examples of generally used excipients include, without limitation: saline, buffered saline, dextrose, water-for-infection, glycerol, ethanol, and combinations thereof, stabilizing agents, solubilizing agents and surfactants, buffers and preservatives, tonicity agents, bulking agents, and lubricating agents. The populations of immune effector cells expressing the ADCC Enhancer are typically prepared and cultured ex vivo.

In one method embodiment of the invention, immune effector cells extracted from whole blood from a subject is first infected ex vivo with the recombinant lentivirus (or any other gene therapy vector e.g. herpes virus, adenovirus, AAV, etc.) encoding the ADCC Enhancer of the invention. The infected PBMC cells are then infused back into the same patient subject after confirmation of success in the transfection. The immune effector cells transfused into the patient subject then proceed to find and destroy diseased cells including tumor cells that are coated with antibodies. To practice this method embodiment, the present invention provides a kit to be used by a physician that include the formulated gene constructs of the invention, and, optionally, agents for preparing the PBMC cells as well as instructions. A modified embodiment of this method entails infecting or transfecting a subset of cells from the PBMCs. This can be achieved by culturing the PBMCs under conditions that preferentially support growth of a particular cell type, or by selecting cells through positive or negative selection techniques like fluorescent activated cell sorting or magnetic activated cell sorting, or a combination of both. An alternative method embodiment of the invention is transfection of the DNA construct or RNA for the receptor into PBMCs or purified subsets of cells using standard transfection techniques.

In another embodiment of the invention, the formulations comprise gene constructs encoding the ADCC Enhancer delivered by liposome or nanoparticle-based technology, and may be administered to a subject using modes and techniques known to the skilled artisan. Exemplary modes include, but are not limited to, intravenous injection. Other modes include, without limitation, intratumoral, intradermal, subcutaneous (s.c., s.q., sub-Q, Hypo), intramuscular (i.m.), intraperitoneal (i.p.), intra-arterial, intramedullary, intracardiac, intra-articular (joint), intrasynovial (joint fluid area), intracranial, intraspinal, and intrathecal (spinal fluids). Any known device useful for parenteral injection or infusion of the formulations can be used to effect such administration.

The formulations comprising gene constructs encoding the ADCC Enhancer that are administered to a subject comprise a number of gene constructs or effector cells that are effective for the treatment and/or prophylaxis of the specific indication or disease. Thus, therapeutically effective gene constructs encoding the ADCC Enhancer are administered to subjects when the methods of the present invention are practiced. In general, cell-based formulations are administered that comprise between about $1 \times 10^4$ and about $1 \times 10^{10}$ effector cells. In most cases, the formulation will comprise between about 1×10⁵ and about 1×10⁹ effector cells. However, the number of effector cells administered to a subject will vary between wide limits, depending upon the location, source, identity, extent and severity of the cancer or disease, the age and condition of the individual to be treated, etc. A physician will ultimately determine appropriate dosages to be used.

As used herein, the terms "treat", "treating", and "treatment" have their ordinary and customary meanings, and include one or more of: blocking, ameliorating, or decreasing in severity and/or frequency a symptom of a disease (e.g., cancer) in a subject, and/or inhibiting the growth, division, spread, or proliferation of cancer cells, or progression of cancer (e.g., emergence of new tumors) in a subject. Treatment means blocking, ameliorating, decreasing, or inhibiting by about 1% to about 100% versus a subject in which the methods of the present invention have not been practiced. Preferably, the blocking, ameliorating, decreasing, or inhibiting is about 100%, 99%, 98%, 97%, 96%, 95%, 90%, 80%, 70%, 60%, 50%, 40%, 30%, 20%, 10%, 5% or 1% versus a subject in which the methods of the present invention have not been practiced.

The clinical potency, both as a therapeutic and a prophylactic, of immune effector cells expressing the ADCC Enhancer of the present invention may be optionally enhanced through the use of dendritic cells (DCs). In lymphoid organs, DCs present antigen to T-helper cells, which in turn, regulate immune effectors including CTLs, B cells, macrophages, eosinophils and NK cells. It has been reported that autologous DC engineered to express an HIV antigen or pulsed with exogenous HIV protein was able to prime CTLs in vitro against HIV (Wilson et al., J Immunol., 1999, 162:3070-78). Therefore, in an embodiment of the present invention, DCs are first isolated from the subject patient, and then primed ex vivo through incubation with a source of target antigen(s), e.g., certain tumors-associated antigens or other surface markers of a disease which can be from the subject patient or a foreign source. These DCs are eventually infused back into the patient prior to treatment by autologous CTL and/or other effector cells transfected with the ADCC Enhancing system of the present invention or by formulations comprising DNA and RNA constructs that encode the ADCC Enhancing system. This provides a model of enhanced treatment as well as vaccine using the ADCC Enhancer with the help of DCs.

The invention also provides a kit comprising one or more containers filled with quantities of gene constructs encoding the ADCC Enhancer of the present invention with pharmaceutically acceptable excipients. The kit may also include instructions for use. Associated with the kit may further be a notice in the form prescribed by a governmental agency regulating the manufacture, use or sale of pharmaceuticals or biological products, which notice reflects approval by the agency of manufacture, use or sale for human administration.

IV. Examples (1) Chimeric Receptor

According to embodiments of the present invention, ectodomains of the chimeric ADCC-enhancing receptors were generated in two ways:

(a) Domainal fusion: Based on the predicted amino acid boundaries between the ectodomain and transmembrane region of FcγRI (CD64) and FcγRIII (CD16), a predicted ectodomain of human FcγRI was fused to the transmembrane and intracellular regions of human FcγRIII. DNA and amino acid sequences for the resulting regions in the fusion receptor, SEQ ID NOs:1 and 2, respectively, are shown in FIG. 10. Obviously, DNA sequences besides SEQ ID NO:1 can also translate into the protein of SEQ ID NO:2, and those DNA sequences are also contemplated by the present invention in this and similar instances throughout the application.

Figure 3:
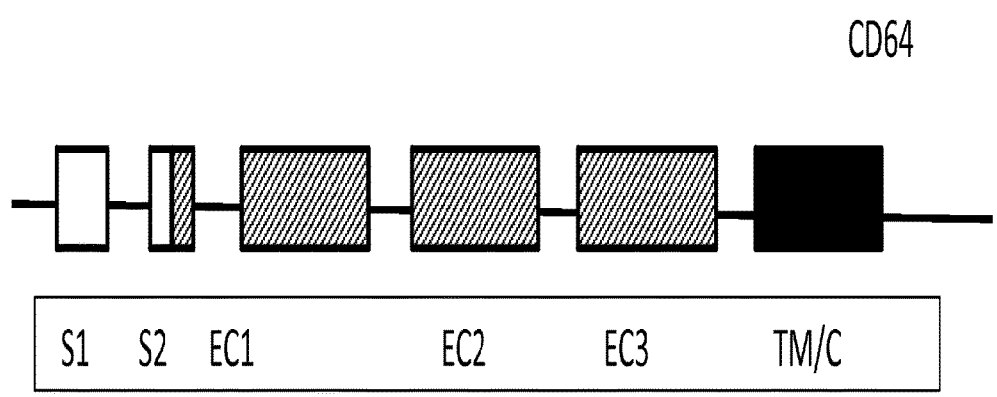
FIG. 3 schematically compares the genomic exon maps of CD16 and CD64: the secretory signal sequence is in white, the extracellular regions are crosshatched and the transmembrane and intracellular regions are in black. Neither the intron nor the exon regions are drawn to scale.
Figure 3:
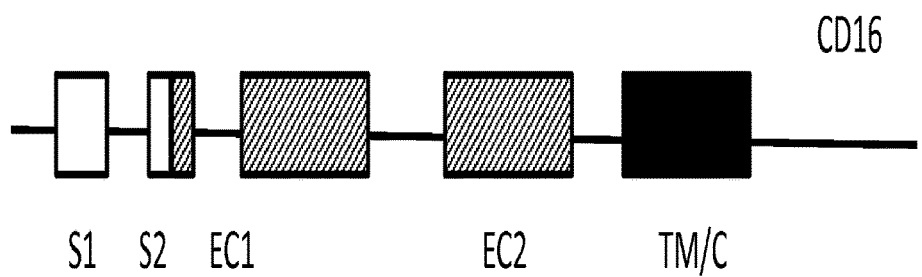

(b) Exon-based fusion: Based on the exon boundaries in FcγRI and FcγRIII, a predicted ectodomain of human FcγRI was fused to the transmembrane and intracellular regions of human FcγRIII. As shown in FIG. 3, both proteins have two exons coding a secretory peptide (S1 and S2), followed by three (CD64) or two (CD16) exons coding for the extracellular regions. Specifically, exons from S1 to EC3 from CD64 were fused with the TM/C exon in CD16. The DNA and amino acid sequences for the resulting regions in the fusion receptor, SEQ ID NOs:3 and 4, respectively, are shown in FIG. 11.

To make the chimeric receptor, cDNA clones of human CD64 and CD16 were obtained from Origene (also available from a variety of other commercial vendors). Flanking primers were designed and synthesized to amplify selected portions of the cDNA and recombinantly combine into one vector using PCR. Primers included restriction sites that facilitated cloning to generate the fusion construct and subcloning into various commercial vectors. Standard restriction digestion and ligation procedures were used throughout.

Figure 4:
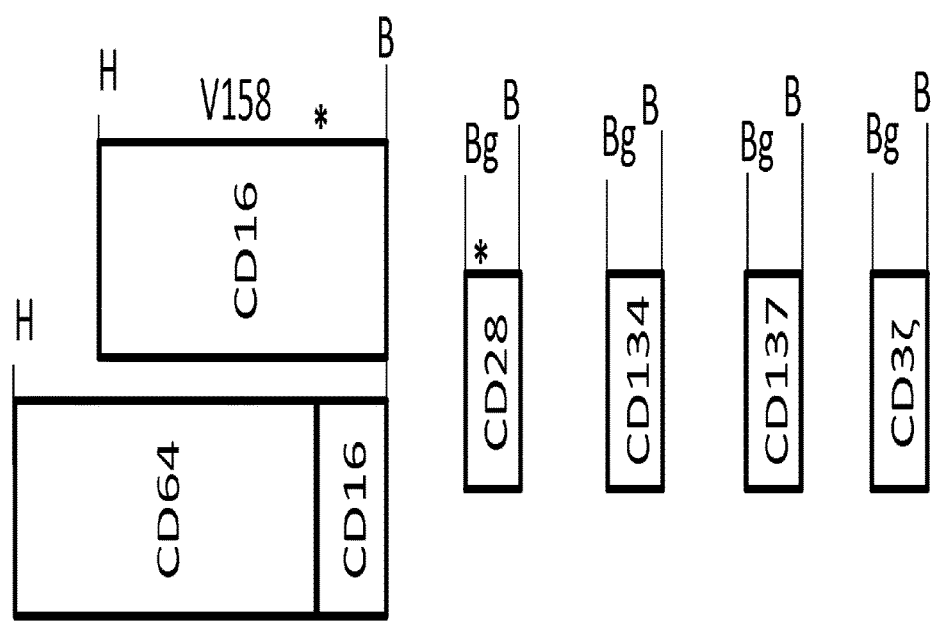
FIG. 4 schematically illustrates the cloning strategy for generating chimeric receptors of the invention according to an embodiment. The flanking letters denotes restriction enzyme sites used during cloning: H-HindIII ("H"), B-BamHI ("B"), and Bg-BglII ("Bg").

Referring now to FIG. 4, once the ectodomain of human CD64 was fused to the transmembrane and intracellular domains of human CD16, they were further fused to various amplification modules found in various human proteins, specifically, CD28 (a.a. 162-202), CD134 (a.a. 213-249), CD137 (a.a. 187-232) and CD3ζ (a.a. 31-142) (all amino acid positions are based on mature protein sequences). Mutations were introduced into the sequence as marked by asterisks as follows: Commercially available CD16 cDNA has a polymorphism that was reverted. In addition, a dileucine motif in CD28 that is known to down-modulate surface expression was mutated. Each module was separated by a -GGATCT- sequence that introduced two spacer amino acids. The DNA and amino acid sequences for the resulting regions in the fusion receptor, SEQ ID NOs:5 and 6, respectively, are shown in FIG. 12. The DNA and amino acid sequences for the entire fusion/chimeric receptor with regions from CD64, CD16 and the four amplification modules described above, SEQ ID NOs:7 to 10, are shown in FIGS. 13 (domainal fusion) and 14 (exon-based fusion), respectively. The "higher-affinity" mutant of human CD16 (V158) was used as control.

Figure 5:
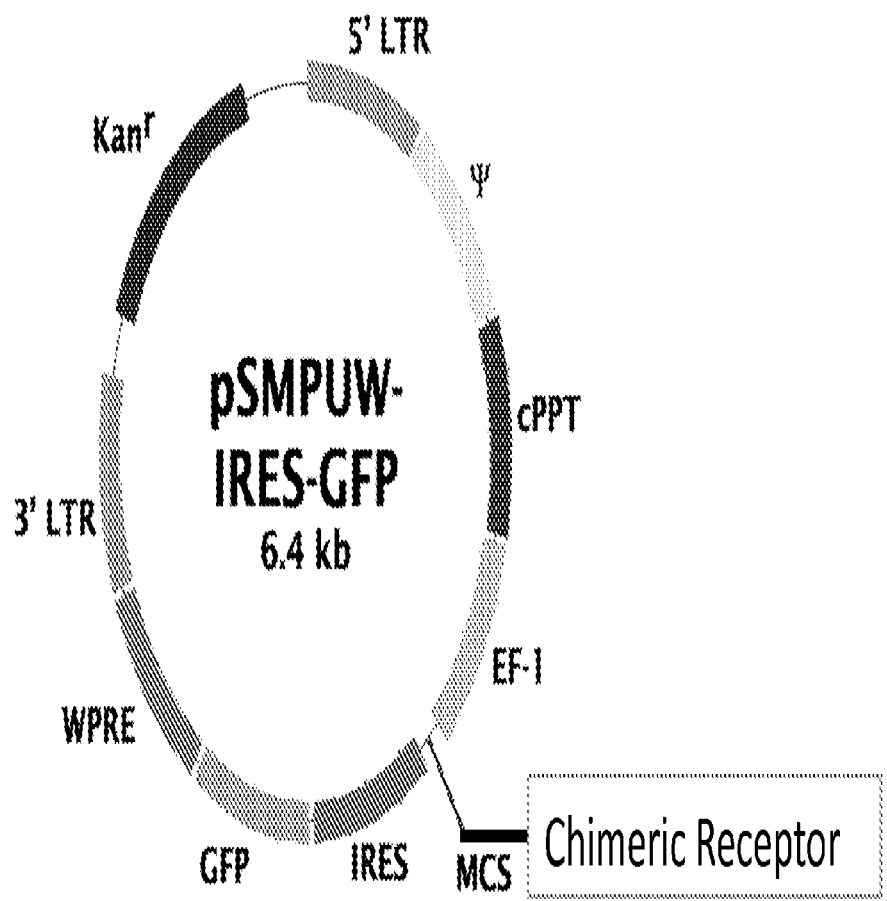
FIG. 5 is a map of a commercially available lentiviral vector used for cloning the receptor according to an embodiment of the invention.
Figure 6:
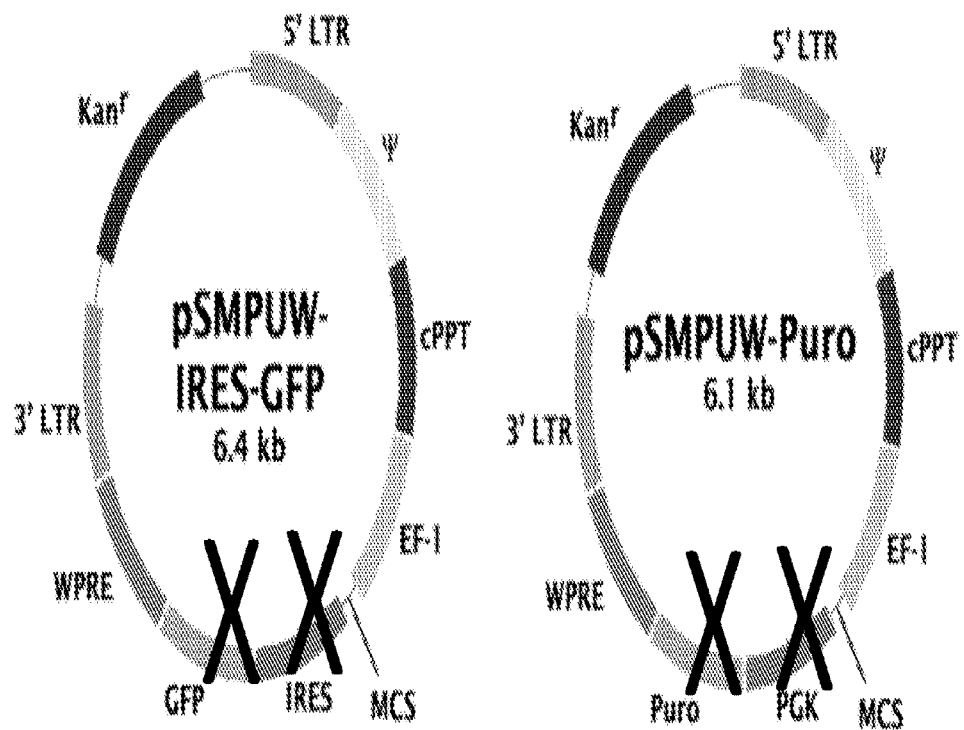
FIG. 6 are maps of alternate vector constructions that can be used for cloning the receptor according to the invention.

The chimeric receptors were then cloned into a commercially available lentiviral vector either with a surrogate marker (e.g., pSMPUW-IRES-GFP shown in FIG. 5) or without (e.g., pSMPUW-puro shown in FIG. 6).

In pSMPUW-IRES-GFP (FIG. 5), GFP expression was linked to the chimeric receptor through an internal ribosome entry site. The puromycin cassette in the pSMPUW-puro vector could be used to select stable and successful clones. For therapeutic uses contemplated by the present invention, however, both the GFP and Puro cassettes would be removed to minimize the size of the vector, as shown being crossed out in FIG. 6. Receptor expression correlated with GFP expression only when the chimeric receptor was generated using exon-based fusion, and therefore, that version of the chimeric receptor became the preferred and default embodiment herein.

(2) Cellular Expression

Figure 7:
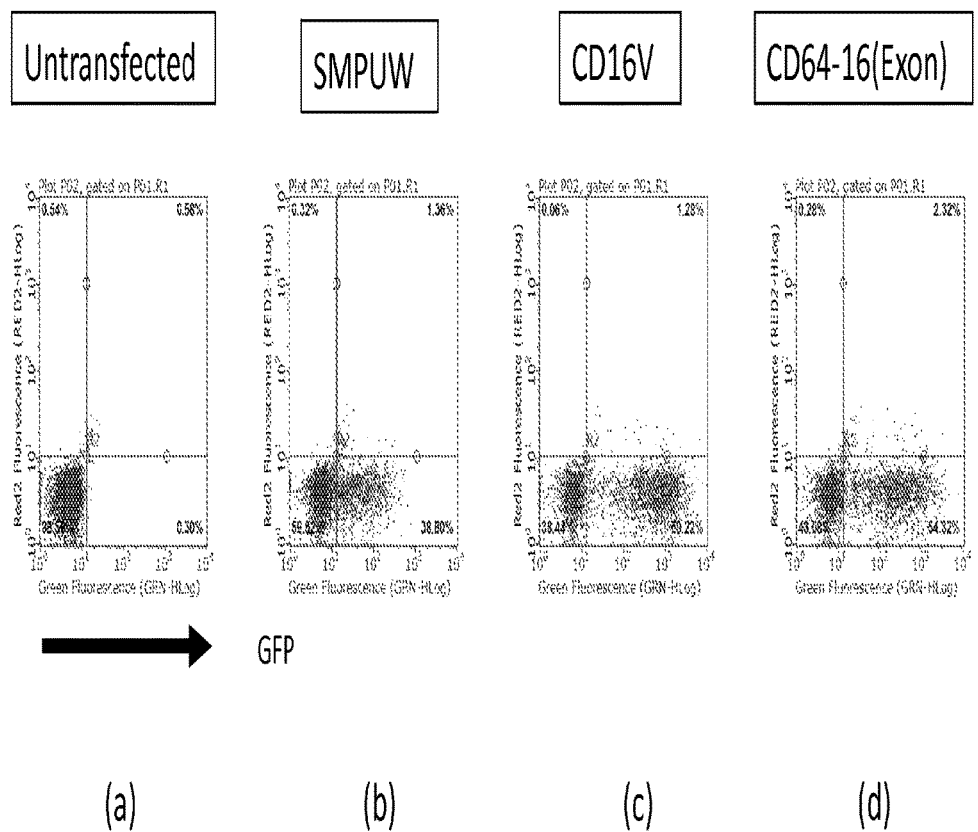
FIG. 7 shows the flow cytometry results of Expi293 cells transfected with (a) negative control, (b) an empty vector, (c) vector expressing CD16V, and (d) vector expressing CD64-16 (Exon) constructs, as measured by the GFP signals emitted by expressed vectors.
Figure 8:
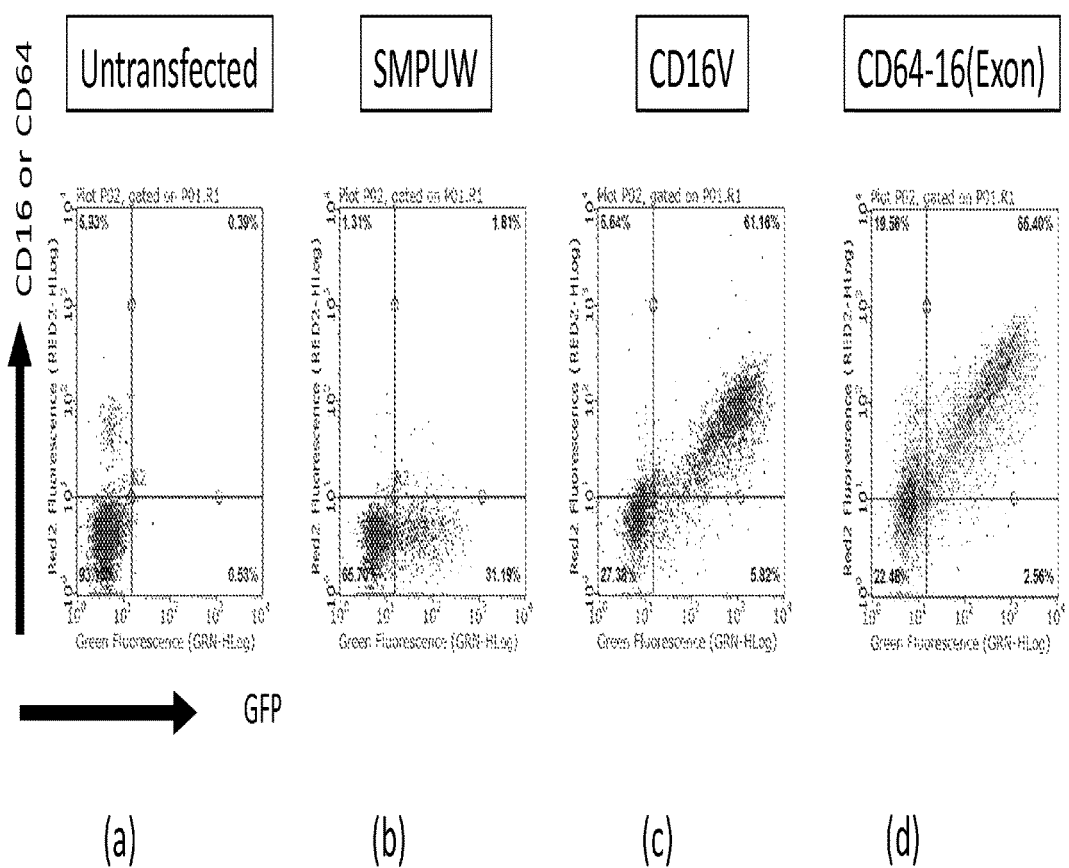
FIG. 8 shows the flow cytometry results of Expi293 cells transfected with (a) negative control, (b) an empty vector, (c) vector expressing CD16V, and (d) vector expressing CD64-16 (Exon) constructs, as measured by fluorescence emitted by fluorescently tagged anti-CD16 (SMPUW and CD16V) or anti-CD64 (CD64-16 based on exon-fusion).

Lentiviral vectors (pSMPUW) were transfected in 293T or Expi293 cells to test expression of the chimeric receptor described above by flow cytometry. Transfection was performed with standard procedures similar to procedures noted above. In the case of pSMPUW-IRES-GFP, transfection was first confirmed through GFP expression 2-3 days after transfection (FIG. 7). Next, expression of the chimeric receptor of the present invention was confirmed by staining the cells with commercially available fluorescently tagged anti-CD16 or anti-CD64 antibodies and measuring resulting fluorescence (FIG. 8).

Since expression of the receptor is linked to GFP expression with the IRES element, receptor expression was correlated to GFP expression. Staining with antibodies was typically achieved by harvesting and washing $10^6$ cells with phosphate buffered saline (PBS) with or without 5% fetal bovine serum (FBS). Cells were incubated for 30 minutes at 4° C. in PBS-FBS in the presence of an appropriate amount of antibodies. Cells were again washed in PBS and analyzed by flow cytometry.

The CD64-CD16 chimeric receptors made using domainal fusion strategy showed much weaker expression (data not shown) than those made using the exon-based fusion.

The pSMPUW vectors were co-transfected with commercially available helper plasmids to make lentiviral particles. Successful transfection was confirmed by analyzing GFP and/or receptor expression.

(3) Therapeutic Affinity

To test the ability of the chimeric receptors in terms of binding human antibodies, cells were first "stained" with commercially available rituximab (Rituxan) antibody as above. Briefly, $10^6$ cells were harvested, washed with PBS and incubated for 30 minutes at 4° C. with 0.1 ug/ml of rituximab. Cells were again washed in PBS and stained with a fluorescently tagged goat anti-human IgG—an antibody that would bind to rituximab or any other human IgG.

Figure 9:
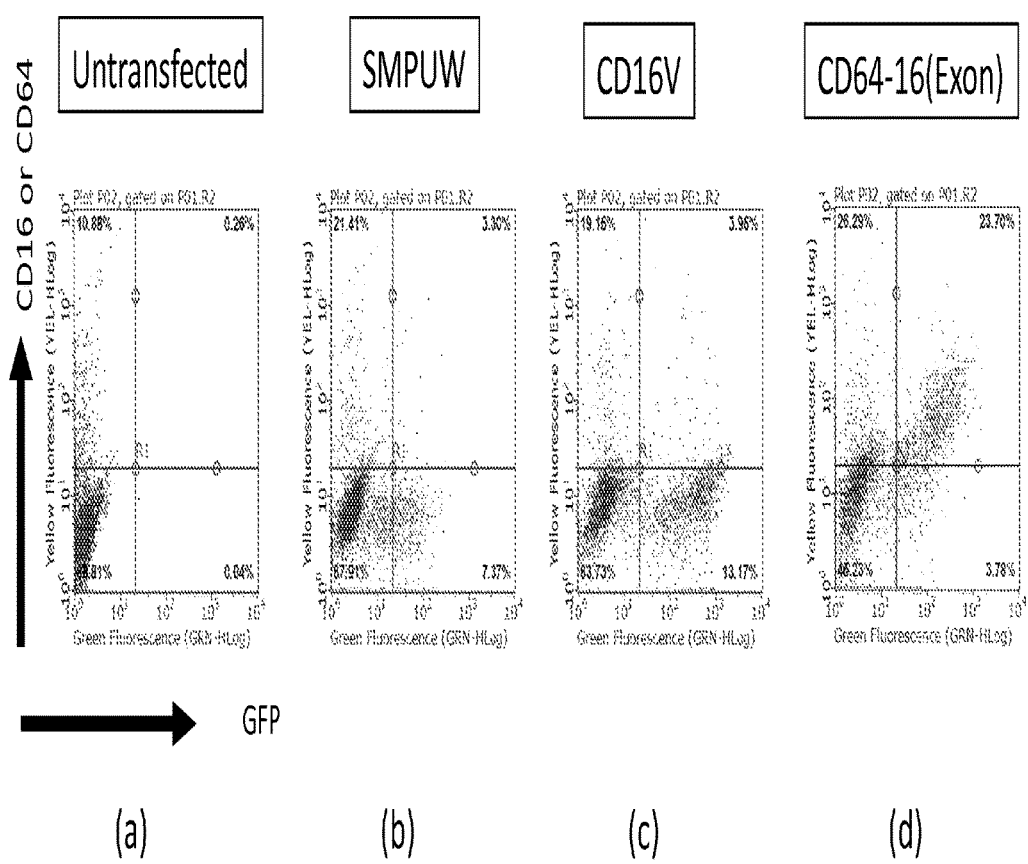
FIG. 9 shows the flow cytometry results of Expi293 cells stained with Rituximab, a therapeutic antibody, after the cells were transfected with (a) negative control, (b) an empty vector, (c) vector expressing CD16V, and (d) vector expressing CD64-16 (Exon) constructs, as measured by fluorescence emitted by fluorescently tagged anti-human IgG.

Under our test conditions, the CD64-CD16 chimeric receptor made with exon-based fusion strategy showed significantly better binding to rituximab than the benchmark V158 version of CD16 (FIG. 9). Similar experiments are carried out with other therapeutic antibodies as well.

An additional level of functionality is the ability to bind antibody-coated target cells. To test, target cells, e.g., Daudi (Burkitt's lymphoma line) cells, are first fluorescently labeled with a cell-tracing reagent, e.g., CellTrace Far Red DDAO-SE. This is typically done by harvesting $5 \times 10^6$ cells, washing them with PBS and then incubating for 5 min with appropriate amount of reagent. The reaction is stopped by adding excess amount of PBS-FBS and then the cells are washed twice with PBS. The labeled cells are then coated with rituximab as described above. Rituximab binds to the cell surface CD20 molecules expressed on Daudi cells. The rituximab-coated cells are then incubated with cells expressing different chimeric receptors for 60 min at 37° C. to test their ability to form heterologous aggregates (GFP+, CellTrace+) as measured by flow cytometry. When using a lentiviral vector without a surrogate marker like GFP, cells expressing the chimeric receptor also need to be stained with a compatible dye e.g. CFSE.

Similar experiments can be done with other cell lines with appropriate targeting antibodies, e.g., Raji or Ramos cells with rituximab, SK-BR-3 (breast carcinoma) cells with trastuzumab, etc.

(4) Immune Effector Cells

After lentiviral particles are made in 293T cells, they can be used to test the functionality of the receptors in T cells. For example, Jurkat (acute T cell leukemia) cells are commonly used surrogate for primary T cells. Functionality of the receptors is revealed in much the same way as described above in 293T cells. Jurkat cells are infected using standard spinoculation method. Typically, $2 \times 10^5$ cells in 100 ul are plated in a 96-well plate. An appropriate amount of viral supernatant is added along with polybrene (4 ug/ml) and centrifuged for 2 hours at 30° C. at 350×g. Cells are analyzed 2 or more days after infection. In the case of $puro^R$-containing lentiviral vectors, stable lines can be generated by selecting the cells with puromycin.

Similar methods are used to infect naïve primary T cells after activation with anti-CD3/CD28. Apart from the analysis similar to Jurkat or 293 cells, the ability of the receptors of the invention can be revealed for activation, proliferation and for triggering cytotoxicity. Typically, to measure proliferation, $10^6$ transduced cells are grown in the presence of 50 IU/ml of IL-2. Rituximab-coated Daudi cells are added to this culture on different days at a ratio of 1:1. As above, other antibody-coated cells can also be used in these experiments. Ideally the target cells (e.g. Daudi) are pretreated with mitomycin C to stall proliferation. T cell proliferation is measured by flow cytometry or other traditional methods e.g. thymidine incorporation, CFSE dilution, etc.

Lysosomal-associated membrane protein-1 (LAMP-1 or CD107a) has been described as a marker of CD8+ T-cell and NK cell degranulation of lytic granules following stimulation. In the co-culture experiments described above, the level of CD107a+ T cells can be analyzed as a measure for degranulation by flow cytometry.

To assess cytotoxicity, T cells are co-cultured for several hours with CellTrace-tagged target cells in the presence of an appropriate therapeutic antibody. Receptor transduction dependent, antibody-dependent depletion of viable target cells are observed. This can be measured by flow cytometry using propidium iodide or 7-AAD.

(5) In Vivo Anti-tumor Activity

Anti-tumor activity is revealed by standard xenograft tumor models using NSG mice from the Jackson lab (see, Shultz et al. *Nat Rev Immunol*. 2007 February; 7(2):118-30). NSG mice lack functional T, B or NK cells and are severely immunocomprised and ideal for engraftment with primary human cells. Other similar mouse strains e.g. NOG mice can also be used.

For instance, luciferase-expressing target tumor cells are injected intraperitoneally (i.p. $0.3 \times 10^6$ cells/mouse). Mice are treated i.p. with rituximab (150 ug) and receptor-transduced T cells ($10^7$ cells) along with 1000-2000 IU of IL-2 after a few days. As controls, either rituximab, the receptor or T cells are excluded in a subset of mice. Tumor engraftment and growth are measured using a Xenogen IVIS system.

Alternate tumor models include injecting $10^7$ Daudi cells s.c. and giving the treatments i.v. Tumor growth is measured directly with calipers or judged by survival.

Similarly experiments are conducted with other cell line antibody combinations including i.p., s.c. or i.v. injection of Raji cells. In the latter, tumor growth is measured by survival.

For the purpose of therapy, the puromycin or the GFP marker would be removed to minimize expression of irrelevant genes.

Another alternate example is to electroporate or transfect mRNA directly. This would be safer than lentiviruses.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

Throughout this application, various publications, patents, and/or patent applications are referenced in order to more fully describe the state of the art to which this invention pertains. The disclosures of these publications, patents, and/or patent applications are herein incorporated by reference in their entireties to the same extent as if each independent publication, patent, and/or patent application was specifically and individually indicated to be incorporated by reference.

Sequence listings and related materials in the ASCII text file named "GHI-002US-Listing_ST25.txt" and created on Apr. 25, 2018 with a size of about 28 kilobytes, is hereby incorporated by reference.

The invention claimed is:

1. A genetic construct that encodes a transmembrane chimeric receptor, comprising a DNA sequence selected from the group consisting of SEQ ID NOs:1, 3, 5, 7, and 9.

2. The genetic construct of claim 1, wherein the encoded transmembrane chimeric receptor comprises the sequence of SEQ ID NO: 2 or the sequence of SEQ ID NO: 10.

3. The genetic construct of claim 1, comprising SEQ ID NO: 9.

* * * * *

SEQUENCE LISTING

<160> NUMBER OF SEQ ID NOS: 10

<210> SEQ ID NO 1
<211> LENGTH: 1032
<212> TYPE: DNA
<213> ORGANISM: artificial
<220> FEATURE:
<223> OTHER INFORMATION: Fusion of human genetic materials

<400> SEQUENCE: 1

```
cttggagaca acatgtggtt cttgacaact ctgctccttt gggttccagt tgatgggcaa      60
gtggacacca caaaggcagt gatcactttg cagcctccat gggtcagcgt gttccaagag     120
gaaaccgtaa ccttgcattg tgaggtgctc catctgcctg ggagcagctc tacacagtgg     180
tttctcaatg gcacagccac tcagacctcg acccccagct acagaatcac ctctgccagt     240
gtcaatgaca gtggtgaata caggtgccag agaggtctct cagggcgaag tgacccata     300
cagctggaaa tccacagagg ctggctacta ctgcaggtct ccagcagagt cttcacggaa     360
ggagaacctc tggccttgag gtgtcatgcg tggaaggata agctggtgta caatgtgctt     420
tactatcgaa atggcaaagc cttaagtttt tccactgga attctaacct caccattctg     480
aaaaccaaca taagtcacaa tggcacctac cattgctcag gcatgggaaa gcatcgctac     540
acatcagcag gaatatctgt cactgtgaaa gagctatttc cagctccagt gctgaatgca     600
tctgtgacat ccccactcct ggaggggaat ctggtcaccc tgagctgtga acaaagttg      660
ctcttgcaga ggcctggttt gcagctttac ttctccttct acatgggcag caagaccctg     720
cgaggcagga acacatcctc tgaataccaa atactaactg ctagaagaga agactctggg     780
ttatactggt gcgaggctgc cacagaggat ggaaatgtcc ttaagcgcag ccctgagttg     840
gagcttcaag tgcttggcct ccagttacca actcctgtct ggtttcatta ccaagtctct     900
ttctgcttgg tgatggtact ccttttttgca gtggacacag gactatattt ctctgtgaag     960
acaaacattc gaagctcaac aagagactgg aaggaccata aatttaaatg gagaaaggac    1020
cctcaagaca aa                                                        1032
```

<210> SEQ ID NO 2
<211> LENGTH: 340
<212> TYPE: PRT
<213> ORGANISM: artificial
<220> FEATURE:
<223> OTHER INFORMATION: fusion of human genetic materials

<400> SEQUENCE: 2

```
Met Trp Phe Leu Thr Thr Leu Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30
```

```
Val Phe Gln Glu Glu Thr Val Thr Leu His Cys Glu Val Leu His Leu
         35                  40                  45

Pro Gly Ser Ser Ser Thr Gln Trp Phe Leu Asn Gly Thr Ala Thr Gln
 50                  55                  60

Thr Ser Thr Pro Ser Tyr Arg Ile Thr Ser Ala Ser Val Asn Asp Ser
 65                  70                  75                  80

Gly Glu Tyr Arg Cys Gln Arg Gly Leu Ser Gly Arg Ser Asp Pro Ile
                 85                  90                  95

Gln Leu Glu Ile His Arg Gly Trp Leu Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Arg Asn Gly Lys Ala Phe
130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
        195                 200                 205

Thr Leu Ser Cys Glu Thr Lys Leu Leu Leu Gln Arg Pro Gly Leu Gln
210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255

Leu Tyr Trp Cys Glu Ala Ala Thr Glu Asp Gly Asn Val Leu Lys Arg
            260                 265                 270

Ser Pro Glu Leu Glu Leu Gln Val Leu Gly Leu Gln Leu Pro Thr Pro
        275                 280                 285

Val Trp Phe His Tyr Gln Val Ser Phe Cys Leu Val Met Val Leu Leu
290                 295                 300

Phe Ala Val Asp Thr Gly Leu Tyr Phe Ser Val Lys Thr Asn Ile Arg
305                 310                 315                 320

Ser Ser Thr Arg Asp Trp Lys Asp His Lys Phe Lys Trp Arg Lys Asp
                325                 330                 335

Pro Gln Asp Lys
            340

<210> SEQ ID NO 3
<211> LENGTH: 1041
<212> TYPE: DNA
<213> ORGANISM: artificial
<220> FEATURE:
<223> OTHER INFORMATION: fusion sequence

<400> SEQUENCE: 3
cttggagaca acatgtggtt cttgacaact ctgctccttt ggggttccagt tgatgggcaa      60 gtggacacca caaaggcagt gatcactttg cagcctccat gggtcagcgt gttccaagag     120
gaaaccgtaa ccttgcattg tgaggtgctc atctgcctg ggagcagctc tacacagtgg     180
tttctcaatg gcacagccac tcagacctcg acccccagct acagaatcac ctctgccagt     240
gtcaatgaca gtggtgaata caggtgccag agaggtctct cagggcgaag tgaccccata     300
```

```
cagctggaaa tccacagagg ctggctacta ctgcaggtct ccagcagagt cttcacggaa    360
ggagaacctc tggccttgag gtgtcatgcg tggaaggata agctggtgta caatgtgctt    420
tactatcgaa atggcaaagc ctttaagttt ttccactgga attctaacct caccattctg    480
aaaaccaaca taagtcacaa tggcacctac cattgctcag gcatgggaaa gcatcgctac    540
acatcagcag gaatatctgt cactgtgaaa gagctatttc cagctccagt gctgaatgca    600
tctgtgacat ccccactcct ggaggggaat ctggtcaccc tgagctgtga acaaagttg     660 ctcttgcaga ggcctggttt gcagctttac ttctccttct acatgggcag caagaccctg    720
cgaggcagga cacatcctc tgaataccaa atactaactg ctagaagaga agactctggg     780
ttatactggt gcgaggctgc cacagaggat ggaaatgtcc ttaagcgcag ccctgagttg    840
gagcttcaag tgcttggttt ggcagtgtca accatctcat cattctttcc acctgggtac    900
caagtctctt tctgcttggt gatggtactc cttttgcag tggacacagg actatatttc     960
tctgtgaaga caaacattcg aagctcaaca agagactgga aggaccataa atttaaatgg   1020
agaaaggacc ctcaagacaa a                                              1041

<210> SEQ ID NO 4
<211> LENGTH: 343
<212> TYPE: PRT
<213> ORGANISM: artificial
<220> FEATURE:
<223> OTHER INFORMATION: fusion protein

<400> SEQUENCE: 4

Met Trp Phe Leu Thr Thr Leu Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30

Val Phe Gln Glu Glu Thr Val Thr Leu His Cys Glu Val Leu His Leu
        35                  40                  45

Pro Gly Ser Ser Ser Thr Gln Trp Phe Leu Asn Gly Thr Ala Thr Gln
    50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Arg Asn Gly Lys Ala Phe
    130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
        195                 200                 205

Thr Leu Ser Cys Glu Thr Lys Leu Leu Leu Gln Arg Pro Gly Leu Gln
    210                 215                 220
```

```
Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
            245                 250                 255

Leu Tyr Trp Cys Glu Ala Ala Thr Glu Asp Gly Asn Val Leu Lys Arg
            260                 265                 270

Ser Pro Glu Leu Glu Leu Gln Val Leu Gly Leu Ala Val Ser Thr Ile
        275                 280                 285

Ser Ser Phe Phe Pro Gly Tyr Gln Val Ser Phe Cys Leu Val Met
    290                 295                 300

Val Leu Leu Phe Ala Val Asp Thr Gly Leu Tyr Phe Ser Val Lys Thr
305                 310                 315                 320

Asn Ile Arg Ser Ser Thr Arg Asp Trp Lys Asp His Lys Phe Lys Trp
                325                 330                 335

Arg Lys Asp Pro Gln Asp Lys
                340
```

```
<210> SEQ ID NO 5
<211> LENGTH: 732
<212> TYPE: DNA
<213> ORGANISM: artificial
<220> FEATURE:
<223> OTHER INFORMATION: Fusion of human DNA

<400> SEQUENCE: 5
aggagtaaga ggagcaggct cctgcacagt gactacatga acatgactcc ccgccgcccc     60
gggcccaccc gcaagcatta ccagccctat gccccaccac gcgacttcgc agcctatcgc    120
tccggatctc ggagggacca gaggctgccc cccgatgccc acaagccccc tgggggaggc    180
agtttccgga cccccatcca agaggagcag gccgacgccc actccaccct ggccaagatc    240
ggatctcgtt tctctgttaa cggggcagaa agaaactcc tgtatatatt caaacaacca    300
tttatgagac cagtacaaac tactcaagag gaagatggct gtagctgccg atttccagaa    360
gaagaagaag gaggatgtga actgggatct agagtgaagt tcagcaggag cgcagacgcc    420
cccgcgtacc agcagggcca gaaccagctc tataacgagc tcaatctagg acgaagagag    480
gagtacgatg tttttggacaa gagacgtggc cgggaccctg agatgggggg aaagccgcag    540
agaaggaaga accctcagga aggcctgtac aatgaactgc agaaagataa gatggcggag    600
gcctacagtg agattgggat gaaaggcgag cgccggaggg gcaaggggca cgatggcctt    660
taccagggtc tcagtacagc caccaaggac acctacgacg cccttcacat gcaggccctg    720
cccccctcgct aa                                                       732
```

```
<210> SEQ ID NO 6
<211> LENGTH: 243
<212> TYPE: PRT
<213> ORGANISM: artificial
<220> FEATURE:
<223> OTHER INFORMATION: fusion protein of human genetic codes

<400> SEQUENCE: 6

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser Gly Ser Arg Arg Asp Gln Arg
        35                  40                  45
```

Leu Pro Pro Asp Ala His Lys Pro Pro Gly Gly Ser Phe Arg Thr
 50                  55                  60

Pro Ile Gln Glu Glu Gln Ala Asp Ala His Ser Thr Leu Ala Lys Ile
 65                  70                  75                  80

Gly Ser Arg Phe Ser Val Lys Arg Gly Lys Lys Leu Leu Tyr Ile
                 85                  90                  95

Phe Lys Gln Pro Phe Met Arg Pro Val Gln Thr Thr Gln Glu Glu Asp
                100                 105                 110

Gly Cys Ser Cys Arg Phe Pro Glu Glu Glu Gly Cys Glu Leu
                115                 120                 125

Gly Ser Arg Val Lys Phe Ser Arg Ser Ala Asp Ala Pro Ala Tyr Gln
130                 135                 140

Gln Gly Gln Asn Gln Leu Tyr Asn Glu Leu Asn Leu Gly Arg Arg Glu
145                 150                 155                 160

Glu Tyr Asp Val Leu Asp Lys Arg Arg Gly Arg Asp Pro Glu Met Gly
                165                 170                 175

Gly Lys Pro Gln Arg Arg Lys Asn Pro Gln Glu Gly Leu Tyr Asn Glu
                180                 185                 190

Leu Gln Lys Asp Lys Met Ala Glu Ala Tyr Ser Glu Ile Gly Met Lys
195                 200                 205

Gly Glu Arg Arg Arg Gly Lys Gly His Asp Gly Leu Tyr Gln Gly Leu
210                 215                 220

Ser Thr Ala Thr Lys Asp Thr Tyr Asp Ala Leu His Met Gln Ala Leu
225                 230                 235                 240

Pro Pro Arg

<210> SEQ ID NO 7
<211> LENGTH: 1758
<212> TYPE: DNA
<213> ORGANISM: artificial
<220> FEATURE:
<223> OTHER INFORMATION: fusion of human DNAs

<400> SEQUENCE: 7

```
atgtggttct tgacaactct gctcctttgg gttccagttg atgggcaagt ggacaccaca    60
aaggcagtga tcactttgca gcctccatgg gtcagcgtgt ccaagaggaa accgtaacc   120
ttgcattgtg aggtgctcca tctgcctggg agcagctcta cacagtggtt ctcaatggc   180
acagccactc agacctcgac ccccagctac agaatcacct ctgccagtgt caatgacagt   240
ggtgaataca ggtgccagag aggtctctca gggcgaagtg acccatacag ctgaaaatc   300
cacagaggct ggctactact gcaggtctcc agcagagtct tcacggaagg agaacctctg   360
gccttgaggt gtcatgcgtg gaaggataag ctggtgtaca atgtgcttta ctatcgaaat   420
ggcaaagcct ttaagttttt ccactggaat tctaacctca ccattctgaa accaacata   480
agtcacaatg gcacctacca ttgctcaggc atgggaaagc atcgctacac atcagcagga   540
atatctgtca ctgtgaaaga gctatttcca gctccagtgc tgaatgcatc tgtgacatcc   600
ccactcctgg aggggaatct ggtcaccctg agctgtgaaa caagttgct cttgcagagg   660
cctggttgc agctttactt ctccttctac atgggcagca agaccctgcg aggcaggaac   720
acatcctctg ataccaaat actaactgct agaagagaag actctgggtt atactggtgc   780
gaggctgcca cagaggatgg aaatgtcctt aagcgcagcc tgagttggag gcttcaagtg   840
cttggcctcc agttaccaac tcctgtctgg tttcattacc aagtctcttt ctgcttggtg   900
atggtactcc ttttgcagt ggacacagga ctatatttct ctgtgaagac aaacattcga   960
```

```
agctcaacaa gagactggaa ggaccataaa tttaaatgga gaaaggaccc tcaagacaaa    1020
ggatctagga gtaagaggag caggggcggg cacagtgact acatgaacat gactccccgc    1080
cgccccgggc ccacccgcaa gcattaccag ccctatgccc caccacgcga cttcgcagcc    1140
tatcgctccg gatctcggag ggaccagagg ctgcccccg atgccacaa gcccctggg     1200 ggaggcagtt tccggacccc catccaagag gagcaggcca cgcccactc caccctggcc    1260 aagatcggat ctcgtttctc tgttaaacgg ggcagaaaga aactcctgta tatattcaaa    1320
caaccattta tgagaccagt acaaactact caagaggaag atggctgtag ctgccgattt    1380
ccagaagaag aagaaggagg atgtgaactg ggatctagag tgaagttcag caggagcgca    1440
gacgcccccg cgtaccagca gggccagaac cagctctata cgagctcaa tctaggacga    1500 agagaggagt acgatgtttt ggacaagaga cgtggccggg accctgagat ggggggaaag    1560
ccgcagagaa ggaagaaccc tcaggaaggc ctgtacaatg aactgcagaa agataagatg    1620
gcggaggcct acagtgagat tgggatgaaa ggcgagcgcc ggaggggcaa ggggcacgat    1680
ggcctttacc agggtctcag tacagccacc aaggacacct cgacgccct tcacatgcag    1740 gccctgcccc ctcgctaa                                                 1758
```

<210> SEQ ID NO 8
<211> LENGTH: 585
<212> TYPE: PRT
<213> ORGANISM: artificial
<220> FEATURE:
<223> OTHER INFORMATION: fusion protein of human DNAs

<400> SEQUENCE: 8

```
Met Trp Phe Leu Thr Thr Leu Leu Trp Val Pro Val Asp Gly Gln
 1               5                  10                  15

Val Asp Thr Thr Lys Ala Val Ile Thr Leu Gln Pro Pro Trp Val Ser
                20                  25                  30

Val Phe Gln Glu Glu Thr Val Thr Leu His Cys Glu Val Leu His Leu
            35                  40                  45

Pro Gly Ser Ser Ser Thr Gln Trp Phe Leu Asn Gly Thr Ala Thr Gln
        50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Arg Asn Gly Lys Ala Phe
    130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
        195                 200                 205

Thr Leu Ser Cys Glu Thr Lys Leu Leu Leu Gln Arg Pro Gly Leu Gln
    210                 215                 220
```

```
Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
            245                 250                 255

Leu Tyr Trp Cys Glu Ala Ala Thr Glu Asp Gly Asn Val Leu Lys Arg
            260                 265                 270

Ser Pro Glu Leu Glu Leu Gln Val Leu Gly Leu Gln Leu Pro Thr Pro
            275                 280                 285

Val Trp Phe His Tyr Gln Val Ser Phe Cys Leu Val Met Val Leu Leu
290                 295                 300

Phe Ala Val Asp Thr Gly Leu Tyr Phe Ser Val Lys Thr Asn Ile Arg
305                 310                 315                 320

Ser Ser Thr Arg Asp Trp Lys Asp His Lys Phe Lys Trp Arg Lys Asp
            325                 330                 335

Pro Gln Asp Lys Gly Ser Arg Ser Lys Arg Ser Arg Gly Gly His Ser
            340                 345                 350

Asp Tyr Met Asn Met Thr Pro Arg Arg Pro Gly Pro Thr Arg Lys His
            355                 360                 365

Tyr Gln Pro Tyr Ala Pro Pro Arg Asp Phe Ala Ala Tyr Arg Ser Gly
370                 375                 380

Ser Arg Arg Asp Gln Arg Leu Pro Pro Asp Ala His Lys Pro Pro Gly
385                 390                 395                 400

Gly Gly Ser Phe Arg Thr Pro Ile Gln Glu Glu Gln Ala Asp Ala His
            405                 410                 415

Ser Thr Leu Ala Lys Ile Gly Ser Arg Phe Ser Val Lys Arg Gly Arg
            420                 425                 430

Lys Lys Leu Leu Tyr Ile Phe Lys Gln Pro Phe Met Arg Pro Val Gln
            435                 440                 445

Thr Thr Gln Glu Glu Asp Gly Cys Ser Cys Arg Phe Pro Glu Glu Glu
450                 455                 460

Glu Gly Gly Cys Glu Leu Gly Ser Arg Val Lys Phe Ser Arg Ser Ala
465                 470                 475                 480

Asp Ala Pro Ala Tyr Gln Gln Gly Gln Asn Gln Leu Tyr Asn Glu Leu
            485                 490                 495

Asn Leu Gly Arg Arg Glu Glu Tyr Asp Val Leu Asp Lys Arg Arg Gly
            500                 505                 510

Arg Asp Pro Glu Met Gly Gly Lys Pro Gln Arg Arg Lys Asn Pro Gln
            515                 520                 525

Glu Gly Leu Tyr Asn Glu Leu Gln Lys Asp Lys Met Ala Glu Ala Tyr
            530                 535                 540

Ser Glu Ile Gly Met Lys Gly Glu Arg Arg Arg Gly Lys Gly His Asp
545                 550                 555                 560

Gly Leu Tyr Gln Gly Leu Ser Thr Ala Thr Lys Asp Thr Tyr Asp Ala
            565                 570                 575

Leu His Met Gln Ala Leu Pro Pro Arg
            580                 585

<210> SEQ ID NO 9
<211> LENGTH: 1767
<212> TYPE: DNA
<213> ORGANISM: artificial
<220> FEATURE:
<223> OTHER INFORMATION: fusion of human DNAs

<400> SEQUENCE: 9
atgtggttct tgacaactct gctcctttgg gttccagttg atgggcaagt ggacaccaca    60
```

```
aaggcagtga tcactttgca gcctccatgg gtcagcgtgt tccaagagga aaccgtaacc      120
ttgcattgtg aggtgctcca tctgcctggg agcagctcta cacagtggtt tctcaatggc      180
acagccactc agacctcgac ccccagctac agaatcacct ctgccagtgt caatgacagt      240
ggtgaataca ggtgccagag aggtctctca gggcgaagtg accccataca gctggaaatc      300
cacagaggct ggctactact gcaggtctcc agcagagtct tcacggaagg agaacctctg      360
gccttgaggt gtcatgcgtg aaggataag ctggtgtaca atgtgcttta ctatcgaaat       420
ggcaaagcct ttaagttttt ccactggaat tctaacctca ccattctgaa aaccaacata      480
agtcacaatg gcacctacca ttgctcaggc atgggaaagc atcgctacac atcagcagga      540
atatctgtca ctgtgaaaga gctatttcca gctccagtgc tgaatgcatc tgtgacatcc      600
ccactcctgg aggggaatct ggtcaccctg agctgtgaaa caagttgct cttgcagagg       660 cctggttttgc agctttactt ctccttctac atgggcagca gaccctgcg aggcaggaac      720 acatcctctg aataccaaat actaactgct agaagagaag actctgggtt atactggtgc      780
gaggctgcca cagaggatgg aaatgtcctt aagcgcagcc ctgagttgga gcttcaagtg      840
cttggtttgg cagtgtcaac catctcatca ttctttccac tgggtacca agtctctttc       900 tgcttggtga tggtactcct ttttgcagtg gacacaggac tatatttctc tgtgaagaca      960
aacattcgaa gctcaacaag agactggaag gaccataaat ttaaatggag aaaggaccct     1020
caagacaaag gatctaggag taagaggagc agggcgggc acagtgacta catgaacatg       1080
actccccgcc gccccgggcc cacccgcaag cattaccagc cctatgcccc accacgcgac     1140
ttcgcagcct atcgctccgg atctcggagg accagaggc tgccccccga tgcccacaag      1200
cccccgtggg gaggcagttt ccggaccccc atccaagagg agcaggccga cgcccactcc     1260
accctggcca agatcggatc tcgtttctct gttaaacggg gcagaaagaa actcctgtat     1320
atattcaaac aaccatttat gagaccagta caaactactc aagaggaaga tggctgtagc     1380
tgccgatttc cagaagaaga agaaggagga tgtgaactgg gatctagagt gaagttcagc     1440
aggagcgcag acgccccgc gtaccagcag ggccagaacc agctctataa cgagctcaat     1500
ctaggacgaa gagaggagta cgatgttttg gacaagagac gtggccggga ccctgagatg     1560
gggggaaagc cgcagagaag gaagaaccct caggaaggcc tgtacaatga actgcagaaa     1620
gataagatgg cggaggccta cagtgagatt gggatgaaag cgagcgccg gaggggcaag     1680 gggcacgatg gcctttacca gggtctcagt acagccacca aggacaccta cgacgccctt     1740
cacatgcagg ccctgccccc tcgctaa                                        1767
```

<210> SEQ ID NO 10
<211> LENGTH: 588
<212> TYPE: PRT
<213> ORGANISM: artificial
<220> FEATURE:
<223> OTHER INFORMATION: fusion protein of human DNAs

<400> SEQUENCE: 10

```
Met Trp Phe Leu Thr Thr Leu Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30

Val Phe Gln Glu Glu Thr Val Thr Leu His Cys Glu Val Leu His Leu
        35                  40                  45

Pro Gly Ser Ser Ser Thr Gln Trp Phe Leu Asn Gly Thr Ala Thr Gln
    50                  55                  60
Thr Ser Thr Pro Ser Tyr Arg Ile Thr Ser Ala Ser Val Asn Asp Ser
```

```
               65                  70                  75                  80
Gly Glu Tyr Arg Cys Gln Arg Gly Leu Ser Gly Arg Ser Asp Pro Ile
                            85                  90                  95

Gln Leu Glu Ile His Arg Gly Trp Leu Leu Gln Val Ser Ser Arg
                100                 105                 110

Val Phe Thr Glu Gly Glu Pro Leu Ala Leu Arg Cys His Ala Trp Lys
                115                 120                 125

Asp Lys Leu Val Tyr Asn Val Leu Tyr Tyr Arg Asn Gly Lys Ala Phe
130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
                180                 185                 190

Val Leu Asn Ala Ser Val Thr Ser Pro Leu Leu Glu Gly Asn Leu Val
                195                 200                 205

Thr Leu Ser Cys Glu Thr Lys Leu Leu Leu Gln Arg Pro Gly Leu Gln
210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255

Leu Tyr Trp Cys Glu Ala Ala Thr Glu Asp Gly Asn Val Leu Lys Arg
                260                 265                 270

Ser Pro Glu Leu Glu Leu Gln Val Leu Gly Leu Ala Val Ser Thr Ile
            275                 280                 285

Ser Ser Phe Phe Pro Pro Gly Tyr Gln Val Ser Phe Cys Leu Val Met
            290                 295                 300

Val Leu Leu Phe Ala Val Asp Thr Gly Leu Tyr Phe Ser Val Lys Thr
305                 310                 315                 320

Asn Ile Arg Ser Ser Thr Arg Asp Trp Lys Asp His Lys Phe Lys Trp
                325                 330                 335

Arg Lys Asp Pro Gln Asp Lys Gly Ser Arg Ser Lys Arg Ser Arg Gly
                340                 345                 350

Gly His Ser Asp Tyr Met Asn Met Thr Pro Arg Arg Pro Gly Pro Thr
                355                 360                 365

Arg Lys His Tyr Gln Pro Tyr Ala Pro Pro Arg Asp Phe Ala Ala Tyr
                370                 375                 380

Arg Ser Gly Ser Arg Arg Asp Gln Arg Leu Pro Pro Asp Ala His Lys
385                 390                 395                 400

Pro Pro Gly Gly Gly Ser Phe Arg Thr Pro Ile Gln Glu Glu Gln Ala
                405                 410                 415

Asp Ala His Ser Thr Leu Ala Lys Ile Gly Ser Arg Phe Ser Val Lys
                420                 425                 430

Arg Gly Arg Lys Lys Leu Leu Tyr Ile Phe Lys Gln Pro Phe Met Arg
                435                 440                 445

Pro Val Gln Thr Thr Gln Glu Glu Asp Gly Cys Ser Cys Arg Phe Pro
                450                 455                 460

Glu Glu Glu Glu Gly Gly Cys Glu Leu Gly Ser Arg Val Lys Phe Ser
465                 470                 475                 480

Arg Ser Ala Asp Ala Pro Ala Tyr Gln Gln Gly Gln Asn Gln Leu Tyr
                485                 490                 495
```

-continued

```
Asn Glu Leu Asn Leu Gly Arg Arg Glu Glu Tyr Asp Val Leu Asp Lys
            500                 505                 510
Arg Arg Gly Arg Asp Pro Glu Met Gly Gly Lys Pro Gln Arg Arg Lys
            515                 520                 525
Asn Pro Gln Glu Gly Leu Tyr Asn Glu Leu Gln Lys Asp Lys Met Ala
            530                 535                 540
Glu Ala Tyr Ser Glu Ile Gly Met Lys Gly Glu Arg Arg Arg Gly Lys
545                     550                 555                 560
Gly His Asp Gly Leu Tyr Gln Gly Leu Ser Thr Ala Thr Lys Asp Thr
                565                 570                 575
Tyr Asp Ala Leu His Met Gln Ala Leu Pro Pro Arg
            580                 585
```